(12) United States Patent
Stahmann et al.

(10) Patent No.: US 7,757,690 B2
(45) Date of Patent: Jul. 20, 2010

(54) SYSTEM AND METHOD FOR MODERATING A THERAPY DELIVERED DURING SLEEP USING PHYSIOLOGIC DATA ACQUIRED DURING NON-SLEEP

(75) Inventors: Jeffrey E. Stahmann, Ramsey, MN (US); Jesse W. Hartley, Lino Lakes, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1497 days.

(21) Appl. No.: 10/939,711

(22) Filed: Sep. 13, 2004

(65) Prior Publication Data

US 2005/0080461 A1     Apr. 14, 2005

Related U.S. Application Data

(60) Provisional application No. 60/504,709, filed on Sep. 18, 2003.

(51) Int. Cl.
*A61M 16/00* (2006.01)
*A61N 1/18* (2006.01)
(52) U.S. Cl. .................................. 128/204.18; 607/42
(58) Field of Classification Search ........................ None
See application file for complete search history.

(56) References Cited

U.S. PATENT DOCUMENTS

| | | | |
|---|---|---|---|
| 4,365,636 A | 12/1982 | Barker | |
| 4,562,841 A | 1/1986 | Brockway et al. | |
| 4,648,407 A | 3/1987 | Sackner | |
| 4,702,253 A | 10/1987 | Nappholz et al. | |
| 4,813,427 A | 3/1989 | Schlaefke et al. | |
| 4,827,935 A | 5/1989 | Geddes et al. | |
| 4,830,008 A | 5/1989 | Meer | |
| 4,860,766 A | 8/1989 | Sackner | |

(Continued)

FOREIGN PATENT DOCUMENTS

EP     0 940 155 A     9/1999

(Continued)

OTHER PUBLICATIONS

Balaban et al., *Feasibility of Screening for Sleep Apnea Using Pacemaker Impedance Sensor*, NASPE (2001).

(Continued)

*Primary Examiner*—Carl H. Layno
*Assistant Examiner*—Jon-Eric C. Morales
(74) *Attorney, Agent, or Firm*—Hollingsworth & Funk, LLC

(57) ABSTRACT

Systems and methods provide for gathering of patient related data during non-sleep periods and modulating a therapy delivered to the patient during sleep using the gathered data. Data associated with a patient is gathered while the patient is awake. A therapy delivered to the patient during patient sleep is adjusted using the acquired data. The therapy delivered to the patient may include one or more of a respiratory therapy, such as a positive airway pressure (xPAP) therapy, a sleep disordered breathing therapy, a cardiac rhythm management therapy, such as a cardiac overdrive pacing therapy, a medication therapy, or a drug delivery therapy. The therapy delivered to the patient may be optimized using the acquired data.

28 Claims, 14 Drawing Sheets

U.S. PATENT DOCUMENTS

| | | |
|---|---|---|
| 4,928,688 A | 5/1990 | Mower |
| 5,036,849 A | 8/1991 | Hauck et al. |
| 5,101,831 A | 4/1992 | Koyama et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,178,156 A | 1/1993 | Takishima et al. |
| 5,187,657 A | 2/1993 | Forbes |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan et al. |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,483,969 A | 1/1996 | Testerman et al. |
| 5,485,851 A | 1/1996 | Erickson |
| 5,517,983 A | 5/1996 | Deighan et al. |
| 5,522,862 A | 6/1996 | Testerman et al. |
| 5,540,727 A | 7/1996 | Tockman et al. |
| 5,540,732 A | 7/1996 | Testerman |
| 5,545,186 A | 8/1996 | Olson et al. |
| 5,545,202 A | 8/1996 | Dahl et al. |
| 5,549,655 A | 8/1996 | Erickson |
| 5,593,431 A | 1/1997 | Sheldon |
| 5,603,732 A | 2/1997 | Dahl et al. |
| 5,632,281 A | 5/1997 | Rayburn |
| 5,704,345 A | 1/1998 | Berthon-Jones |
| 5,715,812 A | 2/1998 | Deighan et al. |
| 5,720,771 A | 2/1998 | Snell |
| 5,738,102 A | 4/1998 | Lemelson |
| 5,814,087 A | 9/1998 | Renirie |
| 5,836,987 A | 11/1998 | Baumann et al. |
| 5,844,680 A | 12/1998 | Sperling |
| 5,855,593 A | 1/1999 | Olson et al. |
| 5,860,918 A | 1/1999 | Schradi et al. |
| 5,861,011 A | 1/1999 | Stoop |
| 5,876,353 A | 3/1999 | Riff |
| 5,891,023 A | 4/1999 | Lynn |
| 5,911,218 A | 6/1999 | DiMarco |
| 5,916,243 A | 6/1999 | KenKnight et al. |
| 5,944,680 A | 8/1999 | Christopherson et al. |
| 5,957,861 A | 9/1999 | Combs et al. |
| 5,964,778 A | 10/1999 | Fugoso et al. |
| 5,970,975 A | 10/1999 | Estes et al. |
| 5,974,340 A * | 10/1999 | Kadhiresan ................. 607/18 |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,148,814 A | 11/2000 | Clemmer et al. |
| 6,168,568 B1 | 1/2001 | Gavriely |
| 6,212,435 B1 | 4/2001 | Lattner et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,253,103 B1 | 6/2001 | Baura |
| 6,259,947 B1 | 7/2001 | Olson et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,280,462 B1 | 8/2001 | Hauser et al. |
| 6,285,907 B1 | 9/2001 | Kramer et al. |
| 6,286,508 B1 | 9/2001 | Remmers et al. |
| 6,292,693 B1 | 9/2001 | Darvish et al. |
| 6,299,581 B1 | 10/2001 | Rapoport et al. |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,353,759 B1 | 3/2002 | Hartley et al. |
| 6,358,203 B2 | 3/2002 | Bardy |
| 6,361,522 B1 | 3/2002 | Scheiner et al. |
| 6,363,270 B1 | 3/2002 | Colla et al. |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,414,183 B1 | 7/2002 | Sakamoto et al. |
| 6,415,183 B1 | 7/2002 | Scheiner et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,454,719 B1 | 9/2002 | Greenhut |
| 6,459,929 B1 | 10/2002 | Hopper et al. |
| 6,467,333 B2 | 10/2002 | Lewis et al. |
| 6,477,420 B1 | 11/2002 | Struble et al. |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 | 7/2003 | Mansy et al. |
| 6,597,951 B2 | 7/2003 | Kramer et al. |
| 6,600,949 B1 | 7/2003 | Turcott |
| 6,641,542 B2 | 11/2003 | Cho et al. |
| 6,658,292 B2 | 12/2003 | Kroll et al. |
| 6,662,032 B1 | 12/2003 | Gavish et al. |
| 6,694,186 B2 | 2/2004 | Bardy |
| 6,723,055 B2 | 4/2004 | Hoffman |
| 6,731,984 B2 | 5/2004 | Cho et al. |
| 6,741,885 B2 | 5/2004 | Park et al. |
| 6,748,252 B2 | 6/2004 | Lynn et al. |
| 6,752,765 B1 | 6/2004 | Jensen et al. |
| 6,752,766 B2 | 6/2004 | Kowallik et al. |
| 6,773,404 B2 | 8/2004 | Poezevera et al. |
| 6,810,287 B2 | 10/2004 | Zhu et al. |
| 6,881,192 B1 | 4/2005 | Park |
| 6,890,306 B2 | 5/2005 | Poezevera |
| 6,910,481 B2 | 6/2005 | Kimmel et al. |
| 6,964,641 B2 | 11/2005 | Cho et al. |

| | | |
|---|---|---|
| 6,988,498 B2 | 1/2006 | Berthon-Jones et al. |
| 7,025,730 B2 | 4/2006 | Cho et al. |
| 7,062,308 B1 | 6/2006 | Jackson |
| 7,081,095 B2 | 7/2006 | Lynn et al. |
| 7,094,207 B1 | 8/2006 | Koh |
| 7,115,097 B2 | 10/2006 | Johnson |
| 7,130,687 B2 | 10/2006 | Cho et al. |
| 7,155,278 B2 | 12/2006 | King et al. |
| 7,179,229 B1 | 2/2007 | Koh |
| 7,189,204 B2 | 3/2007 | Ni et al. |
| 7,207,945 B2 | 4/2007 | Bardy |
| 7,225,013 B2 | 5/2007 | Geva et al. |
| 7,225,809 B1 | 6/2007 | Bowen et al. |
| 7,252,640 B2 | 8/2007 | Ni et al. |
| 7,395,115 B2 | 7/2008 | Poezevera |
| 2001/0000346 A1 | 4/2001 | Ruton et al. |
| 2001/0031930 A1 | 10/2001 | Roizen et al. |
| 2002/0002327 A1 | 1/2002 | Grant et al. |
| 2002/0058877 A1 | 5/2002 | Baumann et al. |
| 2002/0138563 A1 | 9/2002 | Trivedi |
| 2002/0169384 A1 | 11/2002 | Kowallik et al. |
| 2002/0193685 A1 | 12/2002 | Mate et al. |
| 2002/0193697 A1 | 12/2002 | Cho et al. |
| 2002/0193839 A1 | 12/2002 | Cho et al. |
| 2003/0023184 A1* | 1/2003 | Pitts-Crick et al. .......... 600/547 |
| 2003/0055461 A1 | 3/2003 | Girouard et al. |
| 2003/0073919 A1 | 4/2003 | Hampton et al. |
| 2003/0100925 A1* | 5/2003 | Pape et al. ..................... 607/17 |
| 2003/0105497 A1* | 6/2003 | Zhu et al. ..................... 607/17 |
| 2003/0153953 A1* | 8/2003 | Park et al. ..................... 607/17 |
| 2003/0153954 A1* | 8/2003 | Park et al. ..................... 607/17 |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2004/0002742 A1 | 1/2004 | Florio |
| 2004/0030362 A1 | 2/2004 | Hill et al. |
| 2004/0059240 A1 | 3/2004 | Cho et al. |
| 2004/0073093 A1 | 4/2004 | Hatlestad |
| 2004/0088027 A1* | 5/2004 | Burnes et al. .................. 607/60 |
| 2004/0116981 A1 | 6/2004 | Mazar |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0176695 A1 | 9/2004 | Poezevara |
| 2004/0176809 A1 | 9/2004 | Cho et al. |
| 2004/0186523 A1 | 9/2004 | Florio |
| 2004/0210154 A1 | 10/2004 | Kline |
| 2004/0210155 A1 | 10/2004 | Takemura et al. |
| 2004/0210261 A1 | 10/2004 | King et al. |
| 2005/0039745 A1* | 2/2005 | Stahmann et al. ....... 128/204.18 |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0113710 A1 | 5/2005 | Stahmann et al. |
| 2005/0119711 A1 | 6/2005 | Cho et al. |
| 2005/0142070 A1 | 6/2005 | Hartley et al. |
| 2005/0145246 A1 | 7/2005 | Hartley et al. |
| 2007/0142741 A1 | 6/2007 | Berthon-Jones et al. |
| 2007/0161873 A1 | 7/2007 | Ni et al. |
| 2007/0239057 A1 | 10/2007 | Pu et al. |
| 2007/0282215 A1 | 12/2007 | Ni et al. |

FOREIGN PATENT DOCUMENTS

| | | |
|---|---|---|
| EP | 1 151 718 A | 11/2001 |
| EP | 1317943 | 6/2003 |
| WO | WO9220402 | 11/1992 |
| WO | 99/04841 | 4/1999 |
| WO | WO 00/01438 A | 1/2000 |
| WO | WO 00/17615 | 3/2000 |
| WO | 02/087696 | 11/2002 |
| WO | WO0275744 | 9/2003 |
| WO | WO03075744 | 9/2003 |
| WO | WO2004062485 | 7/2004 |
| WO | WO2005028029 | 3/2005 |

OTHER PUBLICATIONS

Bradley et al., Pathophysiologic and Therapeutic Implications of Sleep Apnea in Congestive Heart Failure, 3 J. Cardiac Failure 223-240 (1996). Abstract only.

Bradley et al., Sleep Apnea and Heart Failure, Park I: Obstructive Sleep Apnea, 107 Circulation 1671-1678 (2003).

Garrigue et al., Night Atrial Overdrive with DDD Pacing Results in a Significant Reduction of Sleep Apnea Episodes and QOL Improvement in Heart Failure Patients, NASPE (2001).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Jais et al., Night Atrial Overdrive with DDD Pacing: a New Therapy for Sleep Apnea Syndrome, NASPE (2000).

Javaheri et al., Sleep Apnea in 81 Ambulatory Male Patients with Stable Heart Failure: Types and Their Prevalences, Consequences, and Presentations, 97 Circulation 2154-2159 (1998).

Olusola et al., Nightcap: Laboratory and home-based evaluation of a portable sleep monitor, 32 Psychophysiology, 32-98 (1995). Abstract only.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N. E. 158-175 (1997).

Roche et al., Screening of Obstructive Sleep Apnea Syndrome by Heart Rate Variability Analysis, 100 Circulation 1411-1455 (1999).

Shahrokh, A Mechanism of Central Sleep Apnea In Patients With Heart Failure,341 N. Engl. J. Med. 949-954 (1999). Abstract only.

Vanninen et al., Cardiac Sympathovagal Balance During Sleep Apnea Episodes, 16 Clin. Physiol. 209-216 (1996). Abstract only.

Waldemark et al., Detection of Apnea using Short Window FFT Technique and Artificial Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993). Abstract only.

1958, Altshule et al., The Effect of Position on Periodic Breathing in Chronic Cardiac Decomposition, New Eng. Journal of Med., vol. 259, No. 22, pp. 1064-1066, Nov. 27, 1958. No copy available.

1987, Dark et al., Breathing Pattern Abnormalities and Arterial Oxygen Desaturation During Sleep in the Congestive Heart Failure Syndrome, Chest, Jun. 1987, 6:833-6. Abstract only.

1990, Hoffman et al., Cheyne-Stokes Respiration in Patients Recovering from Acute Cardiogenic Pulmonary Edema, Chest 1990, 97:410-12.

1999, Junyu et al., Posture Detection Algorithm Using Multi Axis DC-Accelerometer, Pace vol. 22, Apr. 1999. No copy available.

1999, Mansfield, D. et al., Effects of Continuous Positive Airway Pressure on Lung Function in Patients with Chronic Obstructive Pulmonary Disease and Sleep Disordered Breathing, Respirology 365-70, 1999. Abstract only.

2002, Reddel et al., Analysis of Adherence to Peak Flow Monitoring When Recording of Data is Electronic, BMJ 146-147, 2002.

1979, Rees et al., Paroxysmal Nocturnal Dyspnoea and Periodic Respiration, The Lancet, Dec. 22-29, 1979, pp. 1315-1317. Abstract only.

1997, Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Spector et al., Assessing and Managing Dyspnea, The University of Chicago Hospitals. Nursing Spectrum-Career Fitness Online. Self-Study Modules. pp. 1-13. http://nsweb.nursingspectrum.com/.

Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.

Stirbis et al., Optmizing the Shape of Implanted Artificial Pacemakers, Kaunas Medical Institute. Translated from Meditsinskaya Tekhnika, No. 6, pp. 25-27, 1986.

Office Action from U.S. Appl. No. 10/642,998 dated Nov. 23, 2005, 6 pages.

Office Action Response dated Dec. 20, 2005 to office action dated Nov. 23, 2005 from U.S. Appl. No. 10/642,998, 7 pages.

Office Action from U.S. Appl. No. 10/642,998 dated Feb. 8, 2006, 15 pages.

Office Action Response dated May 8, 2006 to office action dated Feb. 8, 2006 from U.S. Appl. No. 10/642,998, 13 pages.

Office Action from U.S. Appl. No. 10/642,998 dated Aug. 10, 2006, 14 pages.

Office Action Response dated Nov. 13, 2006 to office action dated Aug. 10, 2006 from U.S. Appl. No. 10/642,998, 13 pages.

Office Action from U.S. Appl. No. 10/642,998 dated Mar. 15, 2007, 11 pages.

Office Action Response dated May 11, 2007 to office action dated Mar. 15, 2007 from U.S. Appl. No. 10/642,998, 13 pages.

Office Action from U.S. Appl. No. 10/642,998 dated Aug. 20, 2007, 9 pages.

Office Action Response dated Dec. 20, 2007 to office action dated Aug. 20, 2007 from U.S. Appl. No. 10/642,998, 12 pages.

Office Action from U.S. Appl. No. 10/642,998 dated Feb. 29, 2008, 8 pages.

Office Action Response dated Jun. 17, 2008 to office action dated Feb. 29, 2008 from U.S. Appl. No. 10/642,998, 9 pages.

Office Action from U.S. Appl. No. 10/642,998 dated Oct. 1, 2008, 6 pages.

Office Action Response dated Mar. 12, 2009 to office action dated Oct. 1, 2008 from U.S. Appl. No. 10/642,998, 7 pages.

Office Action from U.S. Appl. No. 10/642,998 dated Jun. 8, 2009, 8 pages.

Office Action Response dated Aug. 13, 2009 to office action dated Jun. 8, 2009 from U.S. Appl. No. 10/642,998, 8 pages.

Office Action from U.S. Appl. No. 10/642,998 dated Dec. 9, 2009, 6 pages.

Office Action from U.S. Appl. No. 10/643,203 dated Mar. 31, 2008, 6 pages.

Office Action Response dated Jun. 19, 2008 to office action dated Mar. 31, 2008 from U.S. Appl. No. 10/643,203, 7 pages.

Office Action from U.S. Appl. No. 10/643,203 dated Sep. 22, 2008, 17 pages.

Office Action Response dated Dec. 22, 2008 to office action dated Sep. 22, 2008 from U.S. Appl. No. 10/643,203, 12 pages.

Office Action from U.S. Appl. No. 10/643,203 dated Apr. 29, 2009, 8 pages.

Office Action Response dated Jul. 23, 2009 to office action dated Apr. 29, 2009 from U.S. Appl. No. 10/643,203, 10 pages.

Notice of allowance for U.S. Appl. No. 10/643,203 dated Dec. 17, 2009, 4 pages.

Office Action from European patent application No. 04784602.7 dated May 9, 2007, 3 pages.

Office Action Response to European patent application No. 04784602.7 dated Jan. 10, 2008, 3 pages.

Office Action Response to European patent application No. 04784602.7, dated Apr. 17, 2008, 9 pages.

PCT/US2004/030787 International Search Report dated Sep. 29, 2005, 12 pages.

* cited by examiner

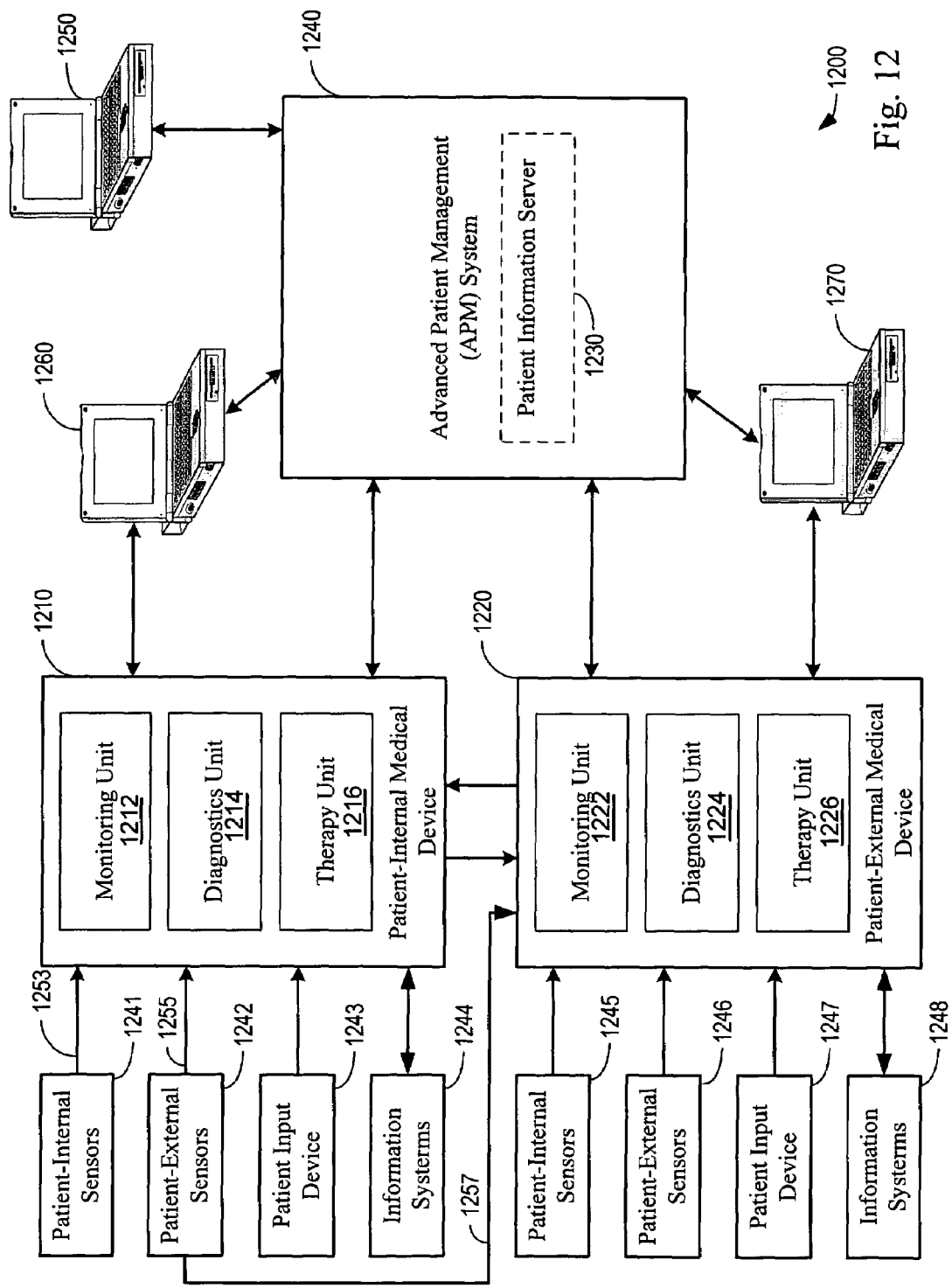

SYSTEM AND METHOD FOR MODERATING A THERAPY DELIVERED DURING SLEEP USING PHYSIOLOGIC DATA ACQUIRED DURING NON-SLEEP

RELATED PATENT DOCUMENTS

This application claims the benefit of Provisional Patent Application Ser. No. 60/504,709, filed on Sep. 18, 2003, to which priority is claimed pursuant to 35 U.S.C. §119(e) and which is hereby incorporated herein by reference in its entirety.

FIELD OF THE INVENTION

The present invention relates generally to medical systems and methods, and more particularly, to medical systems and methods that use data acquired during non-sleep to moderate therapy delivered during sleep.

BACKGROUND OF THE INVENTION

Disordered breathing refers to a wide spectrum of respiratory conditions that involve disruption of the normal respiratory cycle. Although disordered breathing typically occurs during sleep, the condition may also occur while the patient is awake. Unfortunately, disordered breathing is often undiagnosed. If left untreated, the effects of disordered breathing may result in serious health consequences for the patient.

Apnea is a fairly common breathing disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory disorders described above may be observed, including, for example, periodic breathing and Cheyne-Stokes breathing. Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

Disordered breathing affects a significant percentage of people. Sleep disordered breathing is particularly prevalent and is associated with excessive daytime sleepiness, systemic hypertension, increased risk of stroke, angina and myocardial infarction. Respiratory disruption may be particularly serious for patients concurrently suffering from cardiovascular deficiencies, such as congestive heart failure.

Snoring may indicate the presence of sleep disordered breathing. Snoring has been correlated with obstructive sleep apnea. Collapse of the soft tissue in the upper airway during an apnea event causes the airway to vibrate, resulting in snoring. Furthermore, snoring may be correlated to hypertension caused by frequent arousals from sleep, reductions in oxygen saturation, and/or increases in thoracic pressure. Thus, detection of frequent snoring may aid in the diagnosis of patients at risk for hypertension.

Nighttime snoring may cause an increase in inspiratory effort and reduction in tidal volume, leading to frequent arousals from sleep. Frequent arousals from sleep lead to sleep fragmentation, separate from any underlying disordered breathing. Sleep fragmentation leads to fatigue and sleepiness.

SUMMARY OF THE INVENTION

The present invention is directed to systems and methods for gathering patient related data during non-sleep periods and modulating a therapy delivered to the patient during sleep using the gathered data. According to one approach, data associated with a patient is gathered while the patient is awake. A therapy delivered to the patient during patient sleep is adjusted using the acquired data. The therapy includes one or both of a respiratory therapy and a therapy to treat a sleep-related disorder.

For example, the therapy delivered to the patient may include one or more of a respiratory therapy, such as a positive airway pressure (xPAP) therapy, a sleep disordered breathing therapy, a cardiac rhythm management therapy, such as a cardiac overdrive pacing therapy, a medication therapy, or a drug delivery therapy.

The therapy delivered to the patient may be optimized using the acquired data. For example, therapy adjustment and/or optimization may involve performing therapy titration using the acquired data.

A pathological condition may also be detected using the acquired data. A rate of change in the pathological condition may be computed and evaluated. In one approach, a pathological condition may be detected using the acquired data, and a therapy delivered to the patient may be adjusted in response to the detected pathological condition.

The acquired data may include one or more of the following: respiratory data, breathing pattern data, breathing rate data, transthoracic impedance data, heart rate data, heart rate variability (HRV) data, PR interval data, cardiac arrhythmia data, patient activity data, cardiac sound data or pulmonary sound data, contextual data impacting the patient, glucose level data, autonomic nervous system activity data, medication use data, blood pressure data, blood oxygen level data, and/or symptom-based data. Contextual data may include environmental parameters, examples of which include temperature, humidity, pollution, barometric pressure, and body related parameters such as posture and location.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

BRIEF DESCRIPTION OF THE DRAWINGS

FIG. 12 is a block diagram of a medical system that may be used to implement coordinated patient monitoring, diagnosis, and/or therapy in accordance with embodiments of the present invention.

Figure 1A:
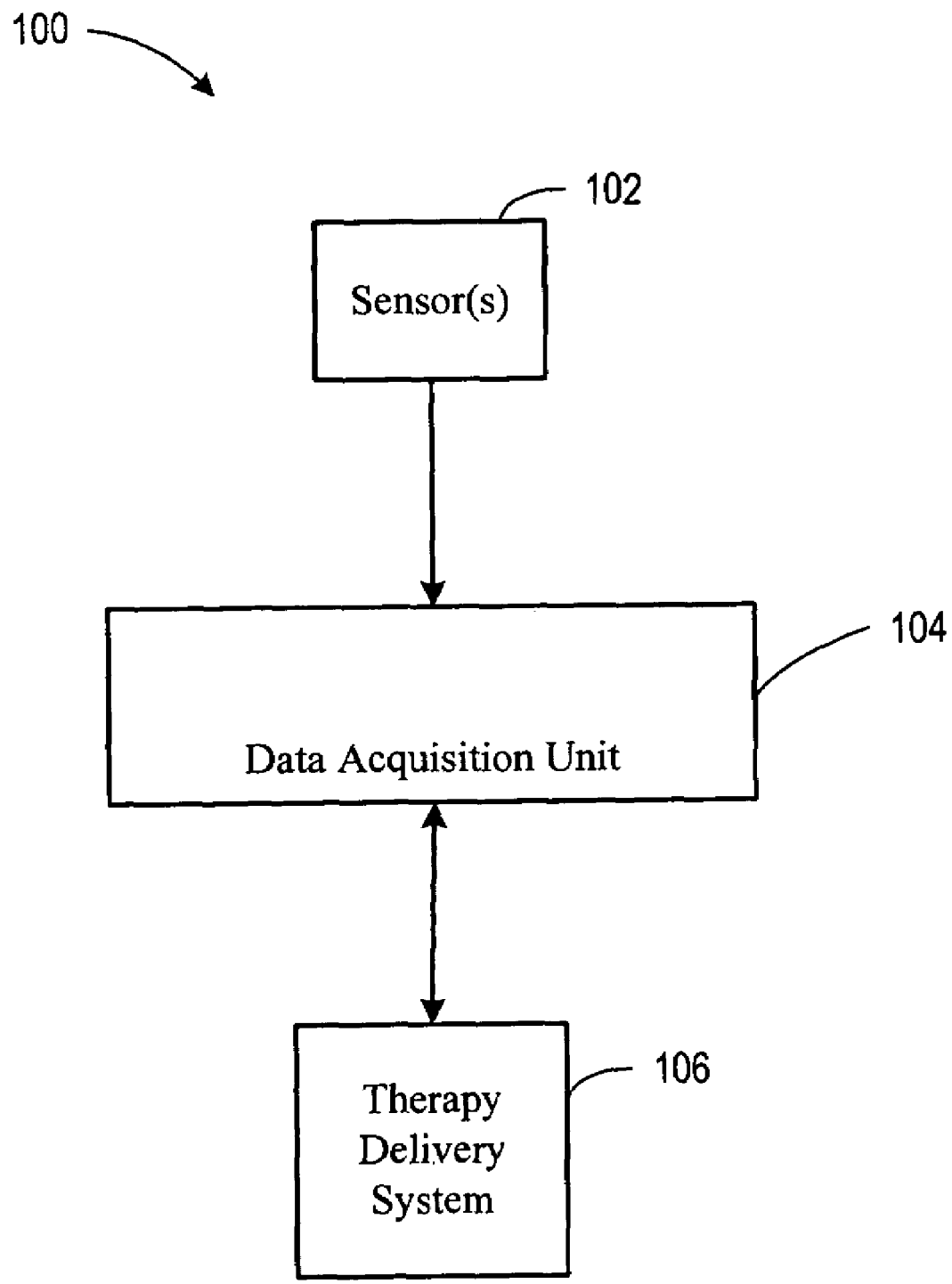
FIGS. 1A, 1B, and 1C are block diagrams of systems providing diurnal data collection to aid nocturnal therapy and diagnosis of sleep disorders in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

A significant percentage of people between the ages of 30 and 60 years experience some symptoms of disordered breathing. Although disordered breathing may occur while the person is awake, it more often occurs during sleep. Sleep disordered breathing is associated with excessive daytime sleepiness, systemic hypertension, increased risk of stroke, angina, and myocardial infarction. Disordered breathing is particularly prevalent among congestive heart failure patients, and may contribute to the progression of heart failure.

Various therapies have been used to treat central and/or obstructive disordered breathing episodes. Obstructive sleep apnea has been associated with prolapse of the tongue and its surrounding structure into the pharynx, thus occluding the respiratory pathway. A commonly prescribed treatment for obstructive apnea is continuous positive airway pressure (CPAP).

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. The term xPAP will be used herein as a generic term for any device that uses a form of positive airway pressure, whether continuous or otherwise. Such devices may also provide for negative airway pressure as necessary, as in the case of treating Cheyne-Stokes breathing, for example.

Figure 1B:
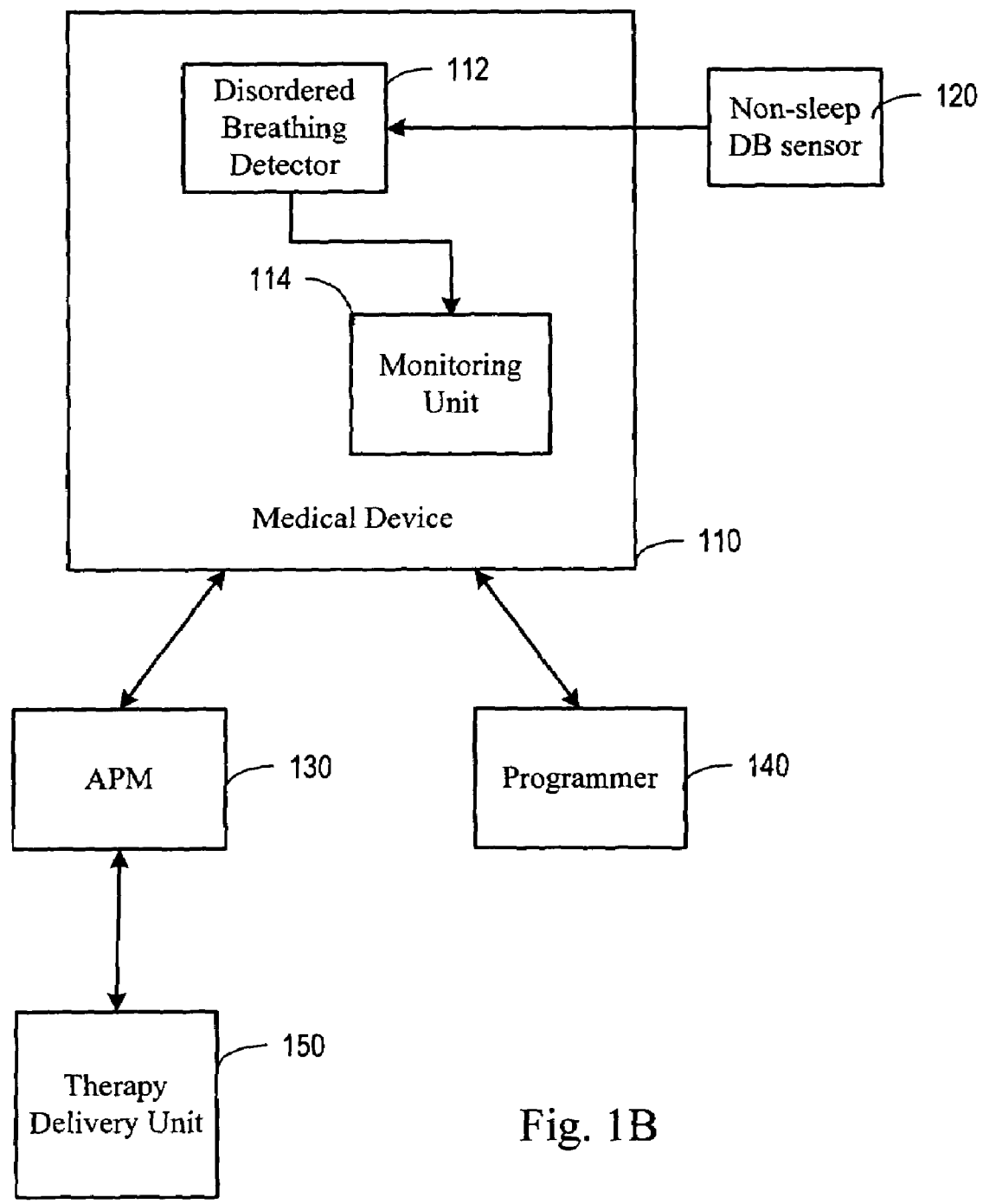
Figure 1C:
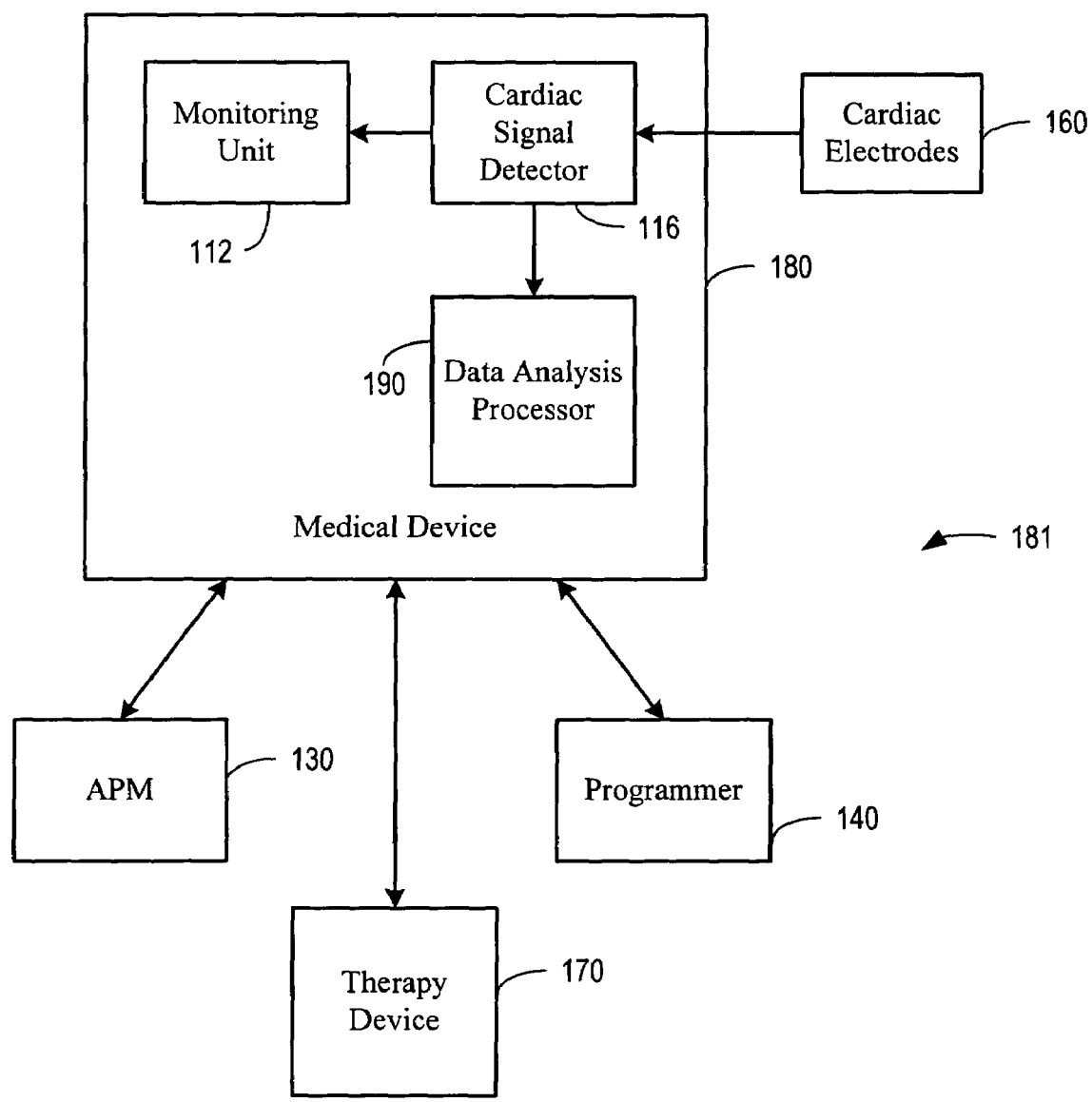

The following discussion, with reference to FIG. 1A-1C, describes embodiments of the invention involving use of diurnal data to aid nocturnal therapy and diagnosis of sleep disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with a further embodiment of the invention, many types of data acquired during non-sleep periods may be used to adjust or enhance therapy during periods of sleep. The data acquired during non-sleep may also be used to provide enhanced diagnostic capabilities for sleep-related disorders. The data acquired during non-sleep may be used, for example, to determine the existence of a condition that occurs during non-sleep periods and is caused, or results from, a sleep-related disorder. The data acquired during non-sleep may determine the extent of the condition, the rate of change of the condition, the amount of change of the condition relative to a baseline, and/or the effect of nocturnal therapy for the condition.

Examples of data acquired during non-sleep that may aid in nocturnal therapy and diagnosis include: transthoracic impedance or other arrangement to assess pathological breathing patterns or conditions such as Cheyne-Stokes breathing, periodic breathing, rapid breathing, respiratory rates, inspiration/expiration intervals, pulmonary function parameters, including for example, forced expiratory volume (FEV) and forced vital capacity (FVC); heart rates, postventricular (PV) intervals and cardiac arrhythmias; activity level; cardiac and pulmonary sounds, (e.g., S3, rales, coughs); environmental data, (e.g., air pollution, humidity); glucose levels; autonomic nervous system activity; medication use, particularly for patients whose use is aperiodic and patient determined (e.g., albuterol for asthma); blood pressure (e.g., average arterial, left atrial end diastolic); blood oxygen level; posture; and symptom-based data (e.g., dyspnea, daytime sleepiness, fatigue, restless leg syndrome (RLS) symptoms).

A variety of sleep-time therapy may be modulated using the data acquired during non-sleep. In one implementation, data acquired during non-sleep may be used to modulate respiration therapy for disordered breathing, e.g., xPAP therapy. In another implementation, data acquired during non-sleep may be used to adjust cardiac overdrive pacing for sleep disordered breathing. In yet another implementation, data acquired during non-sleep may be used to adjust medications used for sleep disorders, e.g., benzodiazepine, tricyclic antidepressants, and theophylline, among others. In another implementation, data acquired during non-sleep may be provided to the patient for behavior modification (e.g., excessive activity too close to sleep time).

Referring to FIG. 1A, a system 100 in accordance with an embodiment of the present invention includes a data acquisition unit 104 configured to acquire data associated with a patient while the patient is awake. The data acquisition unit 104 is coupled to a therapy delivery system 106 configured to adjust a therapy delivered to the patient, during patient sleep, using the acquired data. One or more sensor(s) 102 are used to sense physiological signals useful to the data acquisition unit 104.

As illustrated in FIG. 1B, a system, in accordance with an embodiment of the invention, includes one or more patient-internal and/or patient-external sensors 120 for sensing non-sleep conditions related to disordered breathing. Signals from the one or more sensors 120 may be acquired by a disordered breathing detector 112 in a patient-internal or patient-external medical device 110 and used to detect non-sleep episodes of disordered breathing. In one implementation, respiratory signals, sensed using the sensor 120, such as a transthoracic impedance sensor, are detected during non-sleep periods.

The respiration signals may be stored in the memory of a monitoring unit 114 within the medical device 110. The respiration signals may be trended, displayed, and/or transmitted to another device, such as an advanced patient management (APM) system 130 or a programmer 140 periodically or on command.

The non-sleep respiration signals may be used to modify therapy for sleep disordered breathing. In one example, the APM system 130 analyzes the non-sleep respiration signals to determine the presence and/or severity of non-sleep time periodic breathing. The APM system 130 may use information about disordered breathing, such as the onset or extent of periodic and/or Cheyne-Stokes breathing during non-sleep periods, to determine the optimal sleep time xPAP therapy for Cheyne-Stokes breathing and/or central sleep apnea therapy. The APM system 130 determines a modified therapy based on the non-sleep respiration signals.

In one example, when periodic and/or Cheyne-Stokes breathing increases or decreases, the pressure delivered by an xPAP therapy unit may be increased or decreased, respectively. In another example, non-sleep time breathing information may be used to modify the initial pressures for an auto-titrating PAP device. The APM system 130 may transmit control signals to a therapy device 150, e.g., a respiration therapy device such as an xPAP device, to modify therapy delivered to the patient during sleep.

Although the example provided in FIG. 1B contemplates the use of the APM system 130 to analyze the non-sleep signals and modify the sleep time delivered therapy, the medical device 110 may perform one or both of these functions.

In another embodiment of the invention, illustrated in FIG. 1C, cardiac information is used to adjust cardiac overdrive pacing prescribed for the treatment of sleep disordered breathing. In this embodiment, a cardiac signal detector unit 116 within an implanted or external device 180 detects cardiac signal information from cardiac electrodes 160, e.g., implanted, subcutaneous, surface electrodes or combinations thereof, during non-sleep periods. The cardiac information may be saved in the memory of a monitoring unit 112 within the medical device 180. The cardiac information may be trended, displayed, or transmitted to another device, such as a programmer 140 or an APM system 130.

The non-sleep period cardiac information may be analyzed to determine an enhanced or optimum cardiac electrical stimulation therapy for sleep disordered breathing. In this example, the non-sleep cardiac information is analyzed in a data analysis unit 190 within the medical device 180. In another implementation, the cardiac information may be analyzed by the APM 130 or other device.

In this example configuration, the medical device 180 uses the cardiac information to adjust timing parameters in an implanted therapy device 170, such as a CRM device. For example, the data analysis unit 190 may determine an average intrinsic heart rate and/or an average PR interval during non-sleep periods. These values may be used to enhance the rate and AV delay used by the cardiac overdrive pacing therapy prescribed to treat sleep disordered breathing in subsequent sleep periods.

In one illustrative configuration, the functions of the medical device 180, including the cardiac signal detector 116, the monitoring unit 112 and/or the data analysis unit 190, and the implanted therapy device 170 are located within an implantable CRM device 181. In this configuration, the data analysis unit 190 receives cardiac signals from implanted cardiac electrodes during non-sleep times. The data analysis unit 190 analyzes the cardiac signals to adjust therapy delivered by the CRM device 181 to treat sleep disordered breathing.

Figure 2:
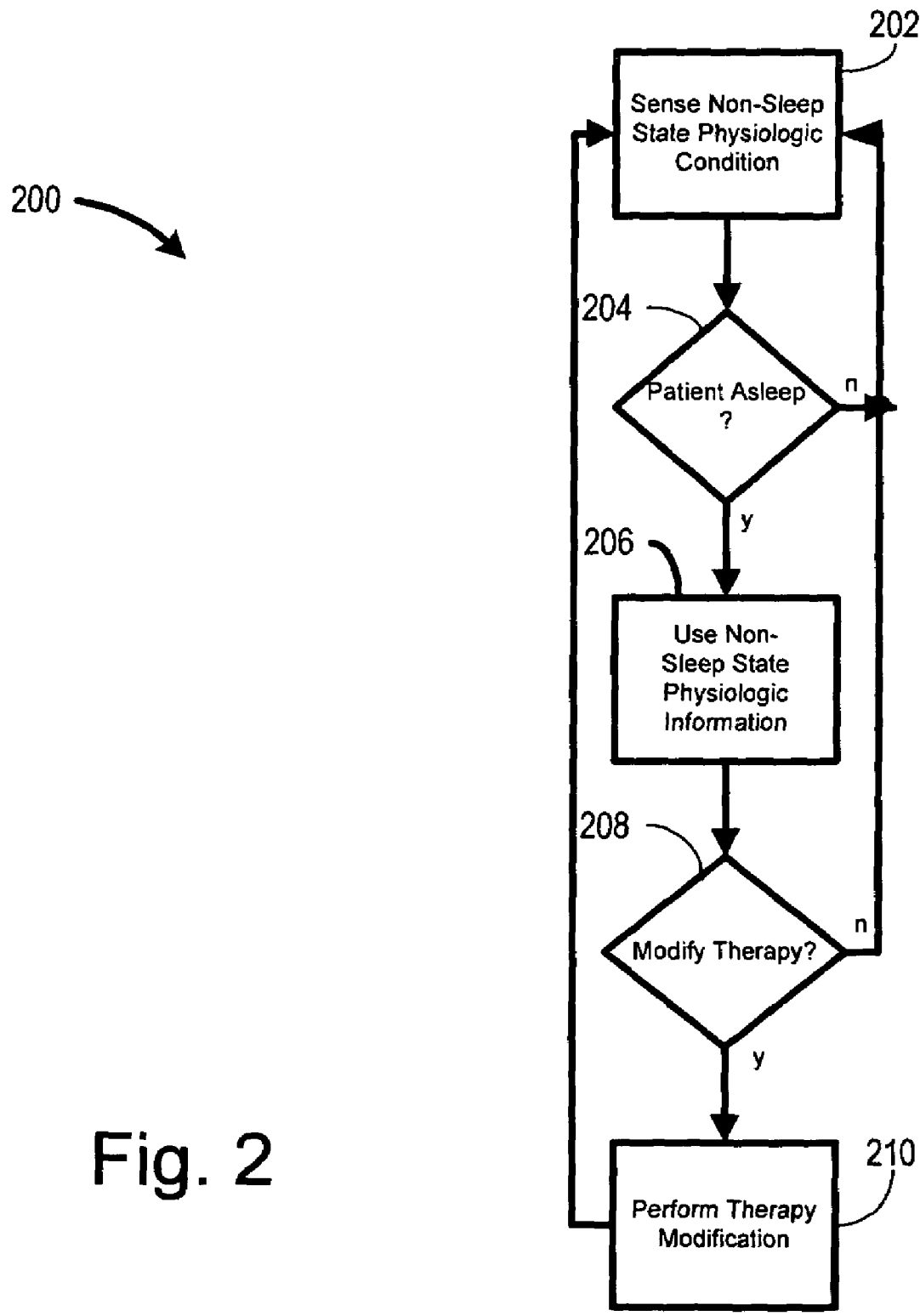
FIG. 2 is a flow chart illustrating of method of moderating sleep therapy using data acquired during non-sleep in accordance with embodiments of the present invention.

FIG. 2 illustrates a method 200 of moderating sleep therapy using physiologic data acquired during non-sleep. A sensor (internal or external to the patient, such as an EEG sensor) is used at block 202 to sense a patient's non-sleep state physiologic condition. The data, trends, or selected parameters may then be stored in memory of an implantable device and/or a patient-external device such as an APM device or server system.

A determination 204 is made that the patient is asleep. If the patient is sleeping, the information stored during the non-sleep period is used at block 206 to, for example, compare the current paced heart rate to the non-sleep intrinsic heart rate. A decision 208 is then made to select continuation of the current therapy or to modify patient therapy based at least in part on physiologic data acquired during non-sleep. If treatment modification is desired, the modification is performed at block 210 before re-starting the method 200.

Figure 3:
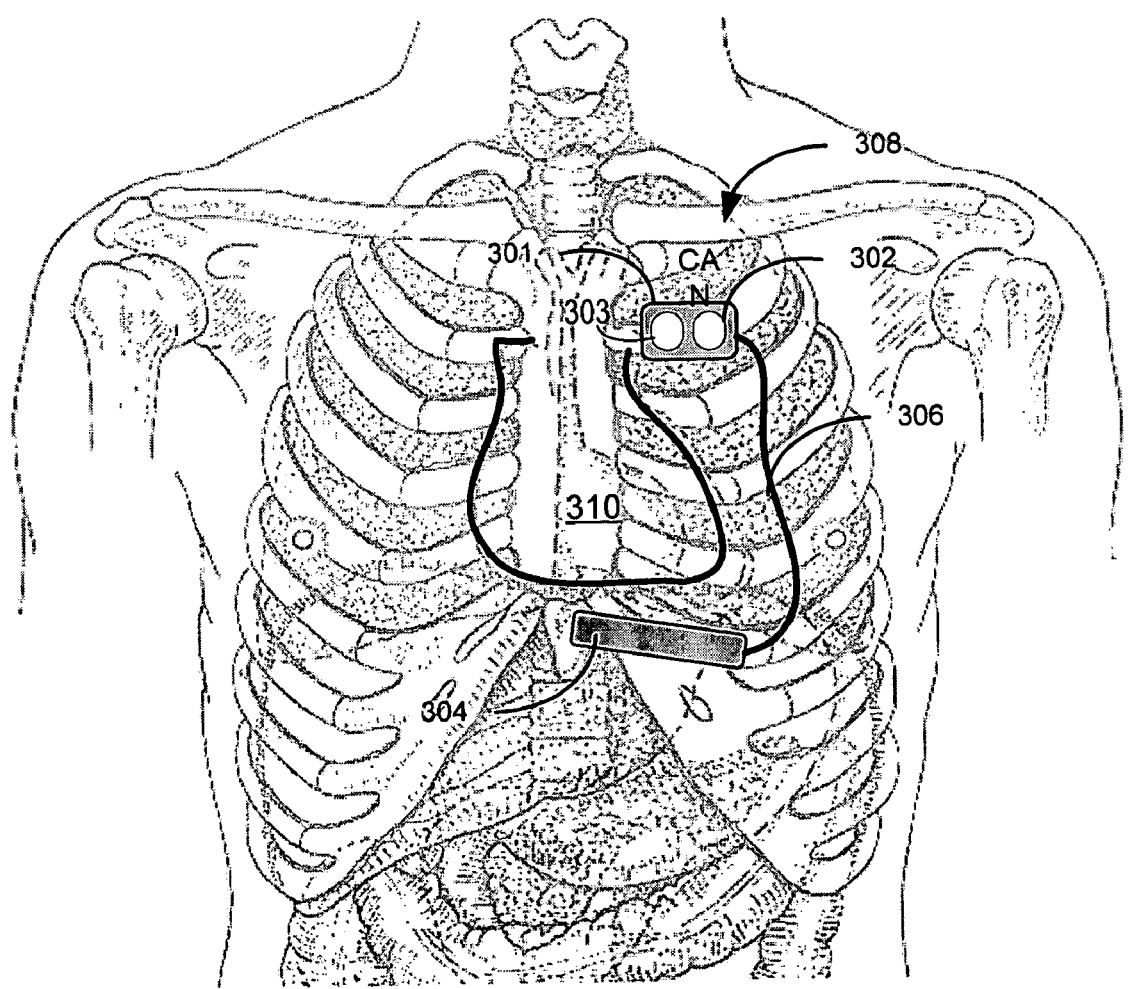
FIG. 3 is a diagram illustrating components of a transthoracic cardiac sensing and/or stimulation device including an electrode array in accordance with an embodiment of the present invention.

In one configuration, as is illustrated in FIG. 3, the invention may be implemented in a patient-internal medical device (PIMD) 308 having componentry arranged about a patient's heart 310. The PIMD 308 includes a first electrode subsystem, including a can electrode 302, and a second electrode subsystem 304. The second electrode subsystem 304 may include a number of electrodes used for sensing and/or electrical stimulation, and may also include non-electrophysiologic sensors.

In various configurations, the second electrode subsystem 304 may include a combination of electrodes. The combination of electrodes of the second electrode subsystem 304 may include coil electrodes, tip electrodes, ring electrodes, multi-element coils, spiral coils, spiral coils mounted on non-conductive backing, screen patch electrodes, and other electrode configurations. A suitable non-conductive backing material is silicone rubber, for example.

The can electrode 302 is positioned on the housing 301 that encloses the PIMD 308 electronics. In one embodiment, the can electrode 302 includes the entirety of the external surface of housing 301. In other embodiments, various portions of the housing 301 may be electrically isolated from the can electrode 302 or from-tissue. The active area of the can electrode 302 may include all or a portion of either the anterior or posterior surface of the housing 301 to direct current flow in a manner advantageous for cardiac sensing and/or stimulation. For example, portions of the housing 301 may be covered with a non-conductive, or otherwise electrically resistive, material to direct current flow. Additional details concerning this and other subcutaneous PIMD embodiments are disclosed in commonly owned, co-pending U.S. Publication No. 2004/0230230, which is hereby incorporated herein by reference.

A PIMD may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties. Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned U.S. patent application Ser. No. 60/462,272, U.S. Publication No. 2004/0230229, and U.S. Publication No. 2004/0230230, each hereby incorporated herein by reference.

Information from a non-cardiac-electrophysiologic sensor 303, such as an EMG sensor, an EEG sensor, an impedance sensor, a blood sensor, an accelerometer, or other sensor, may be used to sense physiologic parameters and/or conditions during non-sleep. The non-cardiac-electrophysiologic sensor 303 may be provided in or on the housing 301, as illustrated in FIG. 3, may be provided as part of the second electrode subsystem 304, and/or may be patient-external. It is also contemplated that the non-cardiac-electrophysiologic sensor 303 may be directly coupled to the housing 301 using an additional lead, or be wirelessly coupled.

In an embodiment of the present invention, sounds, such as hearts sounds and pulmonary sounds, are used to aid in moderating sleep therapy using physiologic information acquired during non-sleep. Because heart sounds are time correlated with respect to the cardiac electrophysiological signals, the non-electrophysiologic signal may provide information about a patient's rhythm state even in the presence of electrical noise and/or electrocardiographic artifacts. A subcutaneous sensor, such as an accelerometer or acoustic transducer, may be used to detect heart sounds. It should also be noted that other sensor derived signals could replace heart sounds. For example, impedance, pulse pressure, blood volume/flow, or cardiac accelerations could be used.

Various types of acoustic sensors may be used to detect heart sounds. Examples of such acoustic sensors include diaphragm based acoustic sensors, MEMS-based acoustic sensors such as a MEMS-based acoustic transducer, fiber optic acoustic sensors, piezoelectric sensors, and accelerometer based acoustic sensors and arrays. These sensors may be used to detect audio frequency (and/or subsonic frequency) pressure waves associated with the heart sounds, and may also be used to detect other non-electrophysiologic cardiac related signals.

Figure 4:
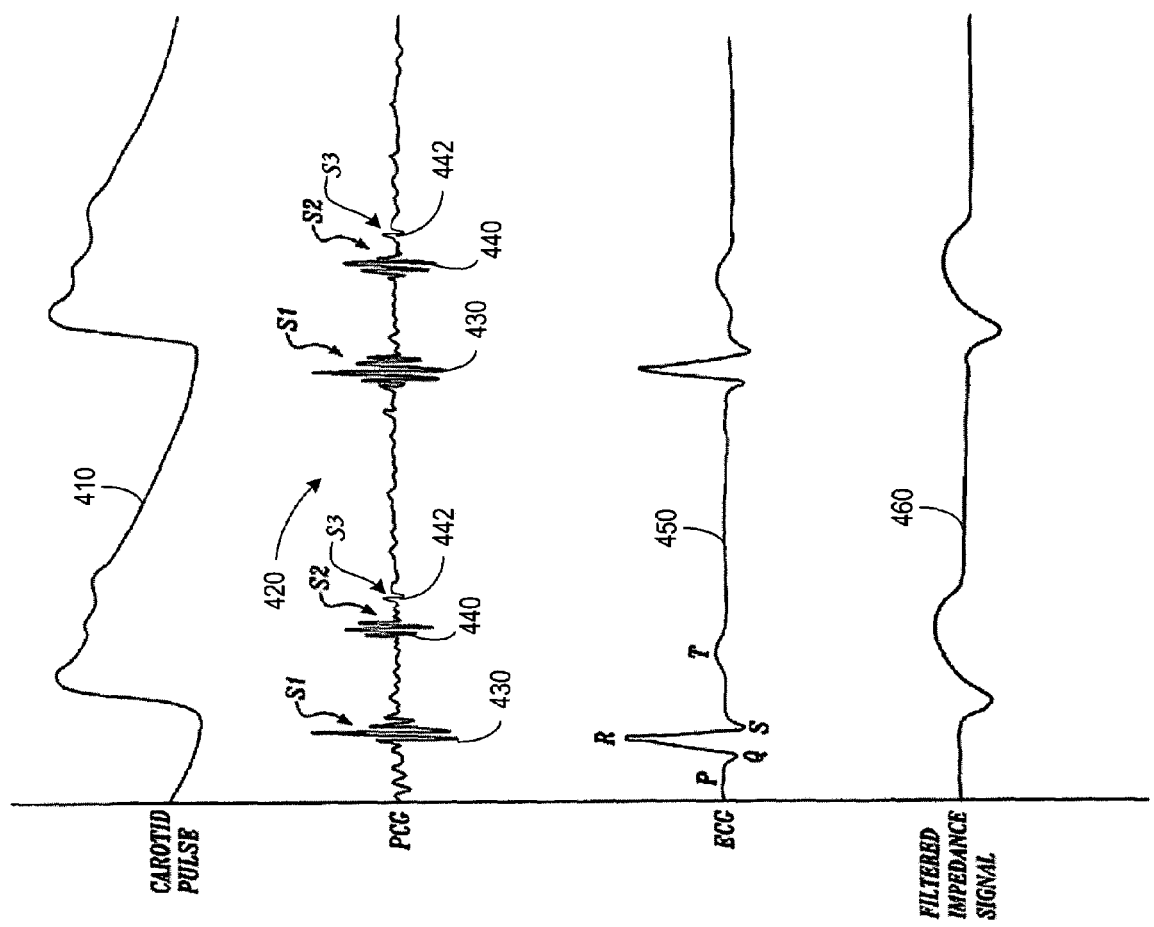
FIG. 4 is a pictorial diagram of a carotid pulse waveform, a phonocardiogram (PCG) waveform, an electrocardiogram (ECG) waveform, and a filtered transthoracic impedance signal for two consecutive heartbeats.

The presence of cardiac pulse, or heartbeat, in a patient is generally detected by palpating the patient's neck and sensing changes in the volume of the patient's carotid artery due to blood pumped from the patient's heart. A graph of a carotid pulse signal 410, representative of the physical expansion and contraction of a patient's carotid artery during two consecutive pulses, or heartbeats, is shown at the top of FIG. 4. When the heart's ventricles contract during a heartbeat, a pressure wave is sent throughout the patient's peripheral circulation system. The carotid pulse signal 410 shown in FIG. 4 rises with the ventricular ejection of blood at systole and peaks when the pressure wave from the heart reaches a maximum. The carotid pulse signal 410 falls off again as the pressure subsides toward the end of each pulse.

The opening and closing of the patient's heart valves during a heartbeat causes high-frequency vibrations in the adjacent heart wall and blood vessels. These vibrations may be heard in the patient's body as heart sounds, and may be detected by sensors, as described earlier. A conventional phonocardiogram (PCG) transducer placed on a patient converts the acoustical energy of the heart sounds to electrical energy, resulting in a PCG waveform 420 that may be recorded and displayed, as shown by the graph in the upper middle portion of FIG. 4.

As indicated by the PCG waveform 420 shown in FIG. 4, a typical heartbeat produces two main heart sounds and may produce other sounds depending on pathology. A first heart sound 430, denoted S1, is generated by vibration generally associated with the closure of the tricuspid and mitral valves at the beginning of systole. Typically, the heart sound 430 is about 14 milliseconds long and contains frequencies up to approximately 500 Hz. A second heart sound 440, denoted S2, is generally associated with vibrations resulting from the closure of the aortic and pulmonary valves at the end of systole. While the duration of the second heart sound 440 is typically shorter than the first heart sound 430, the spectral bandwidth of the second heart sound 440 is typically larger than that of the first heart sound 430. A third heart sound 442, denoted S3, is also seen in the PCG waveform 420. The S3 heart sound 442 is created when the ventricles relax and pressure from the filling blood rapidly distends the ventricle. When the stiff, non-compliant ventricular wall reaches its physical limits, it suddenly tenses, and the S3 sound is created. In children an S3 is common and normal. After age 40, it almost always indicates the failing heart in congestive heart failure. As stated earlier, an accelerometer or acoustic transducer may also detect pulmonary sounds, such as rales and/or coughs, to provide physiologic data.

An electrocardiogram (ECG) waveform 450 describes the electrical activity of a patient's heart. The graph in the lower middle portion of FIG. 4 illustrates an example of the ECG waveform 450 for two heartbeats and corresponds in time with the carotid pulse signal 410 and PCG waveform 420 also shown in FIG. 4. Referring to the first shown heartbeat, the portion of the ECG waveform 450 representing depolarization of the atrial muscle fibers is referred to as the "P" wave. Depolarization of the ventricular muscle fibers is collectively represented by the "Q," "R," and "S" waves of the ECG waveform, referred to as the QRS complex. Finally, the portion of the waveform representing repolarization of the ventricular muscle fibers is known as the "T" wave. Between heartbeats, the ECG waveform 450 returns to an isopotential level.

Fluctuations in a patient's transthoracic impedance signal 460 also correlate with blood flow that occurs with each cardiac pulse wave as well as provide breathing information. The bottom graph of FIG. 4 illustrates an example of a filtered transthoracic impedance signal 460 for a patient in which fluctuations in impedance correspond in time with the carotid pulse signal 410, the PCG waveform 420, and ECG waveform 450, also shown in FIG. 4.

Figure 5:
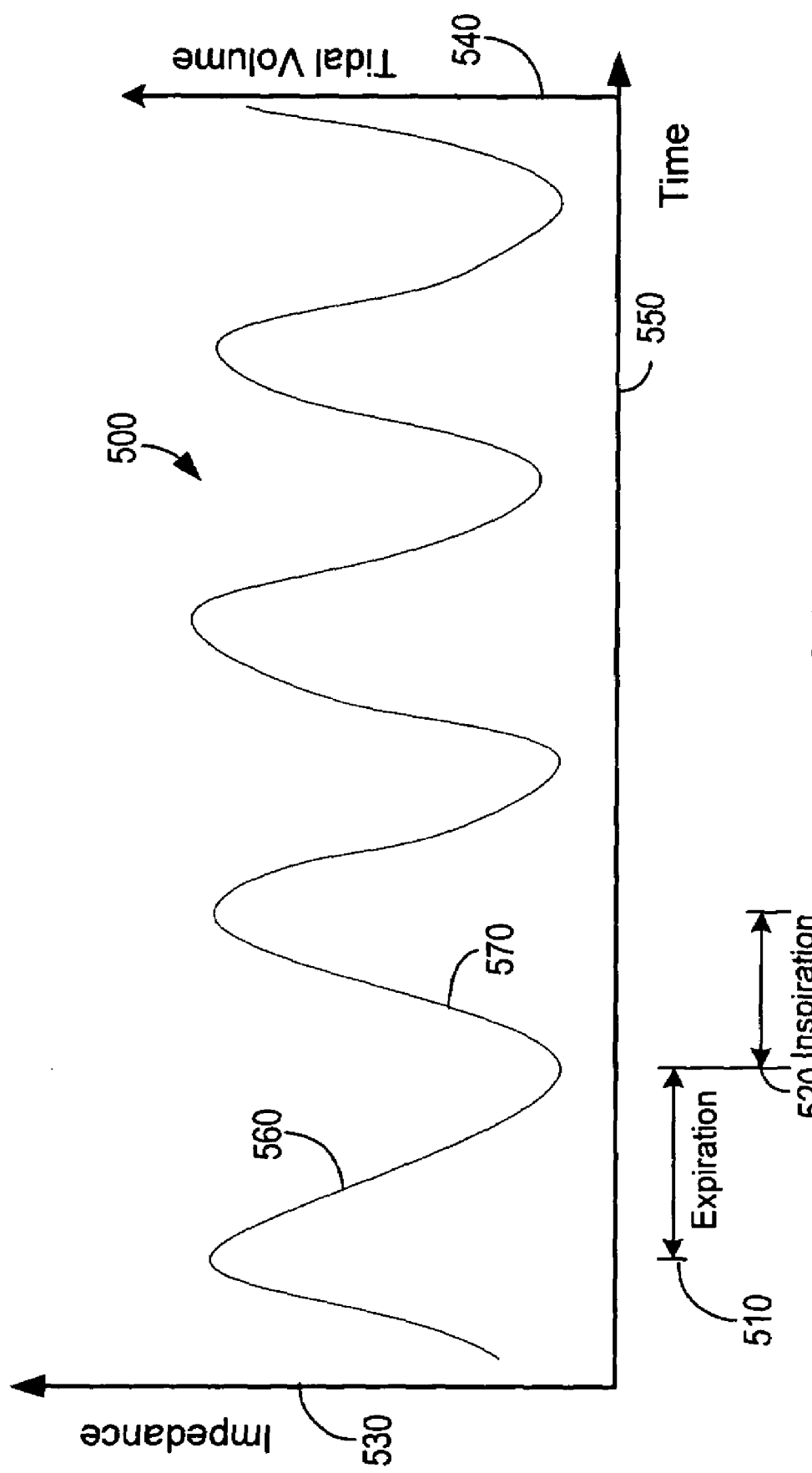
FIG. 5 is a graph of a normal respiration signal measured by a transthoracic impedance sensor that may be utilized for coordinated monitoring, diagnosis and/or therapy in accordance with embodiments of the present invention.

Referring now to FIG. 5, a non-filtered transthoracic impedance signal 500 is illustrated. The impedance signal 500 may be developed, for example, from an impedance sense electrode in combination with a PIMD device. The impedance signal 500 is proportional to the transthoracic impedance, illustrated as an Impedance 530 on the abscissa of the left side of the graph in FIG. 5. The impedance 530 increases 570 during any respiratory inspiration 520 and decreases 560 during any respiratory expiration 510. The impedance signal 500 is also proportional to the amount of air inhaled, denoted a tidal volume 540, illustrated on the abscissa of the right side of the graph in FIG. 5. The variations in impedance during respiration, identifiable as the peak-to-peak variation of the impedance signal 500, may be used to determine the respiration tidal volume 540, corresponding to the volume of air moved in a breath, one cycle of expiration 510 and inspiration 520. A minute ventilation may also be determined, corresponding to the amount of air moved per a minute of time 550 illustrated on the ordinate of the graph in FIG. 5. The impedance signal 500 would also show transient events, such as rales and/or coughs, to provide useful patient condition and prediction information.

Snoring and other episodes of breathing disorders may be determined using the impedance signal 530, and other information available to the sleep detector circuitry. During non-REM sleep, a normal respiration pattern includes regular, rhythmic inspiration—expiration cycles without substantial interruptions. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 6:
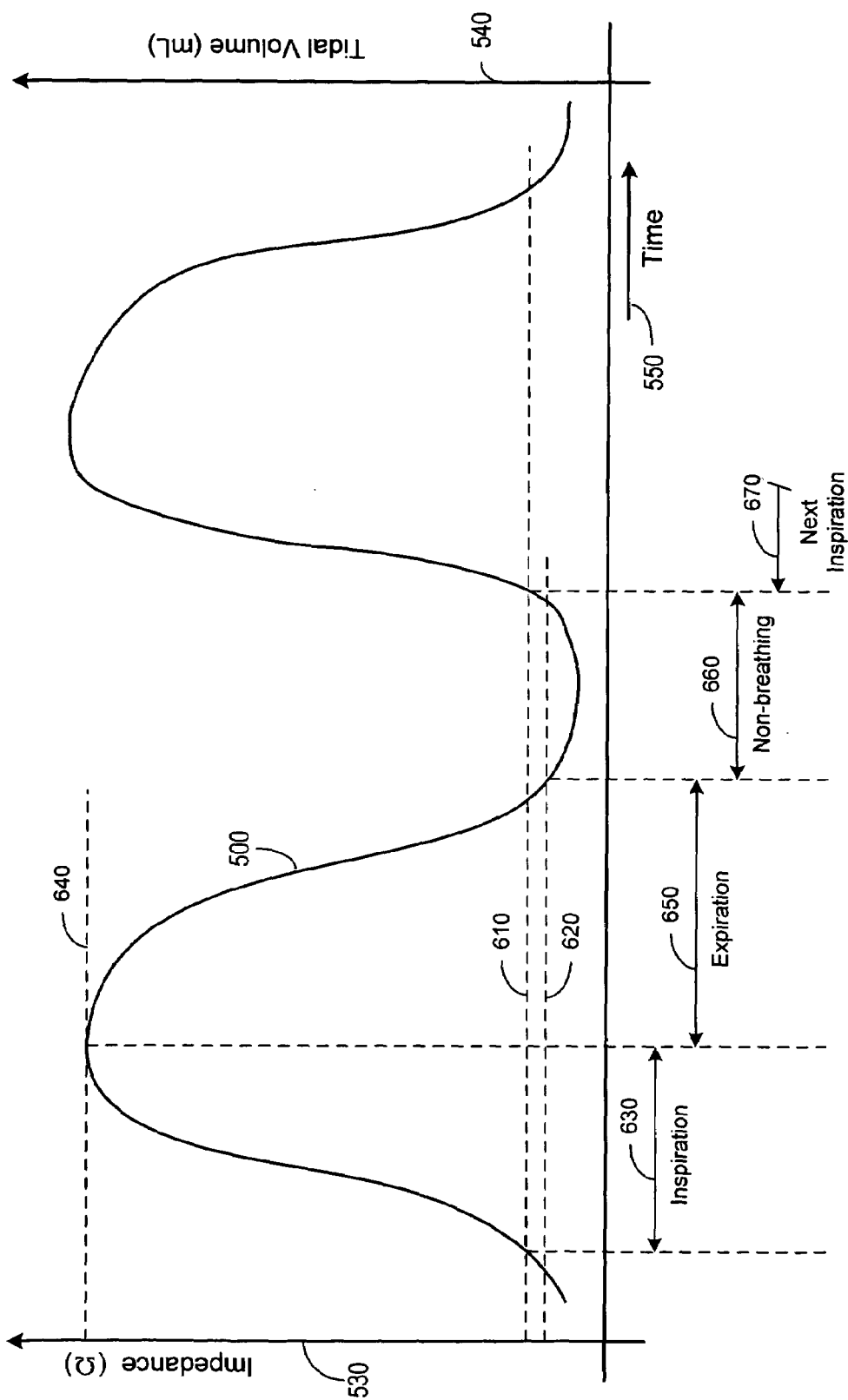
FIG. 6 is a respiration signal graph illustrating respiration intervals used for disordered breathing detection and/or prediction according to embodiments of the invention.
Figure 7:
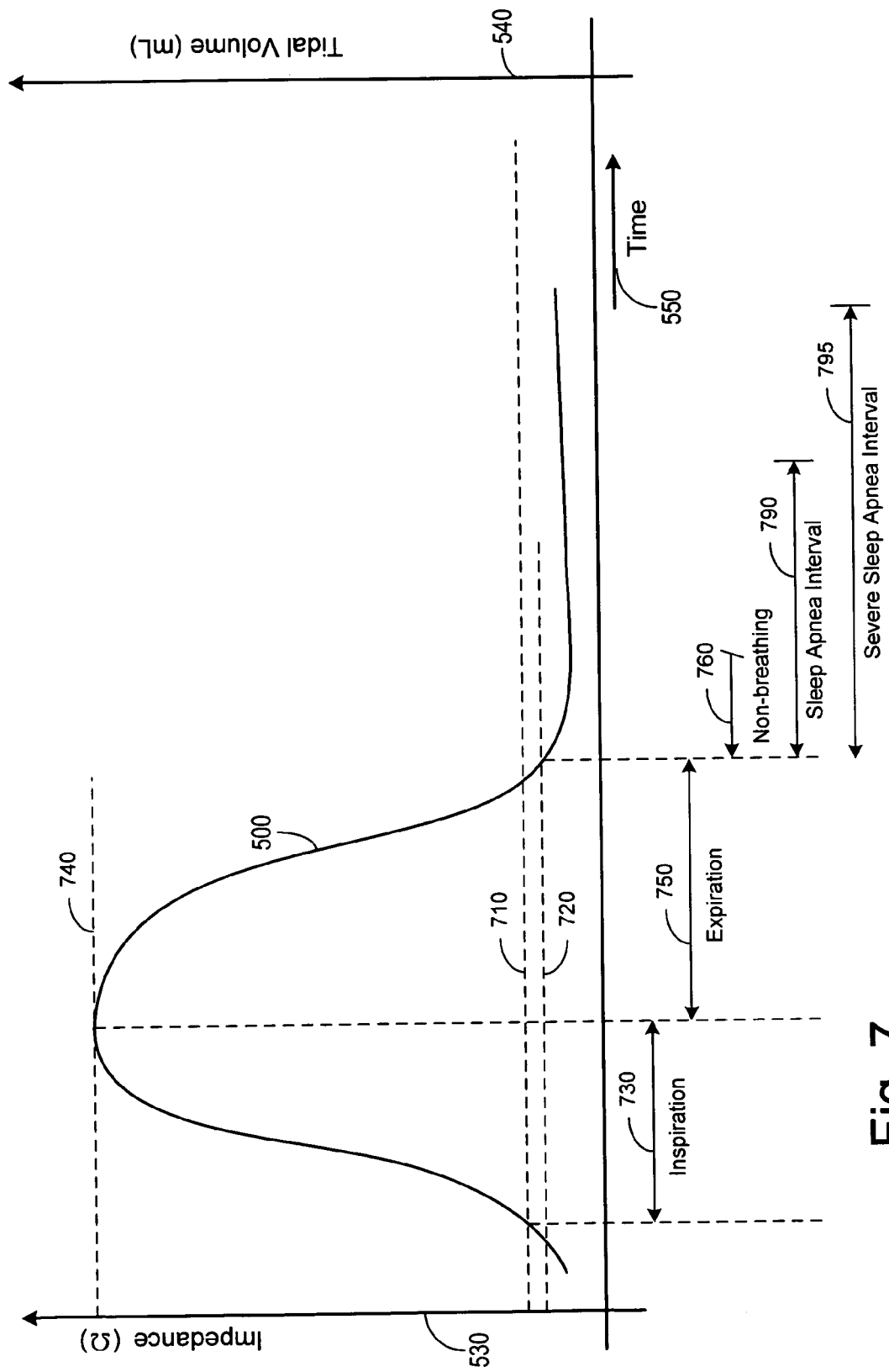
FIG. 7 is a graph of a respiration signal illustrating various intervals that may be used for detection of apnea in accordance with embodiments of the invention.
Figure 8:
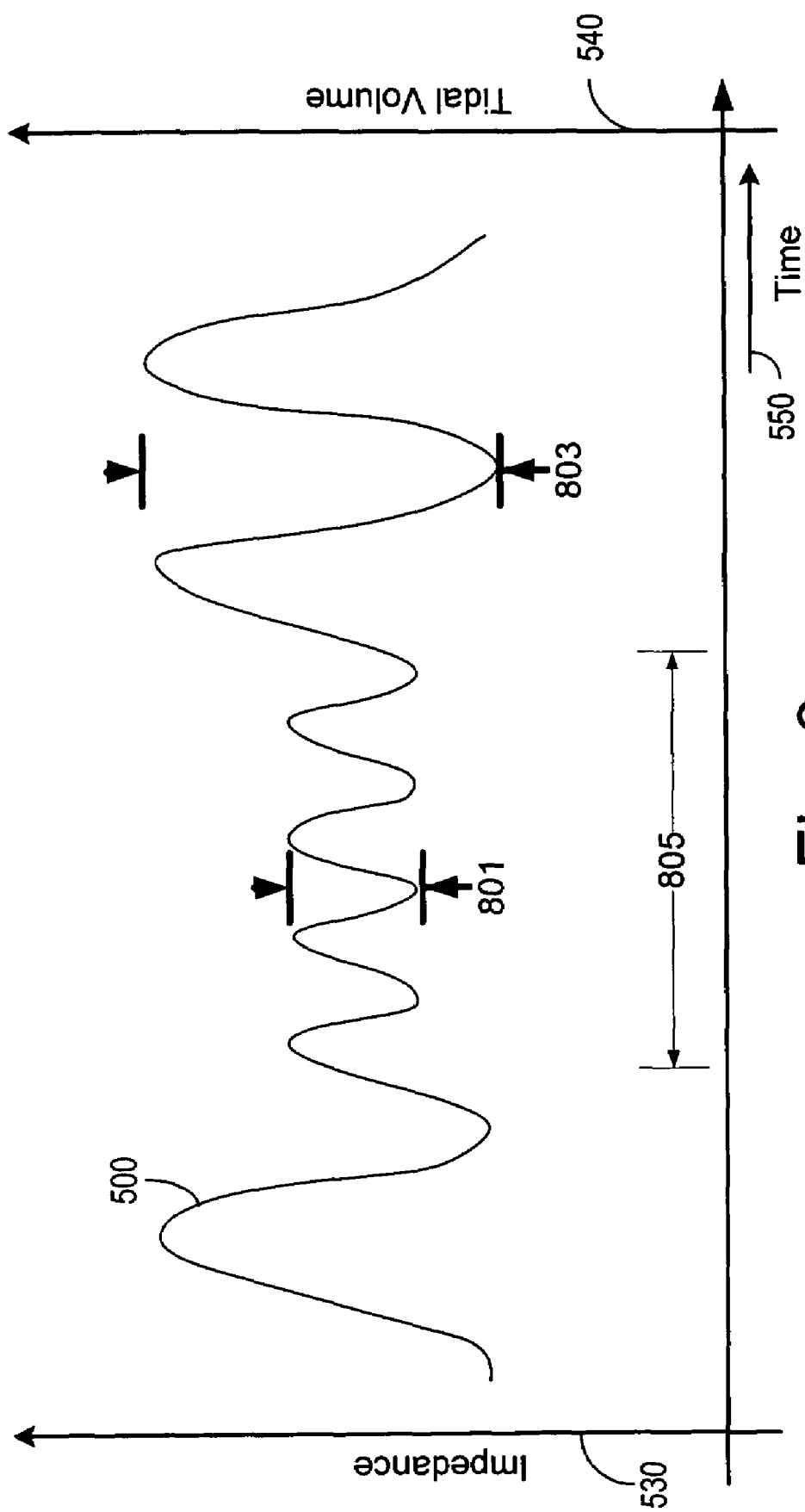
FIG. 8 is a respiration graph illustrating abnormally shallow respiration utilized in detection of disordered breathing in accordance with embodiments of the invention.

FIGS. 6-8 are graphs of transthoracic impedance and tidal volume, similar to FIG. 5 previously described. As in FIG. 5, FIGS. 6-8 illustrate the impedance signal 500 proportional to the transthoracic impedance, again illustrated as Impedance 530 on the abscissa of the left side of the graphs in FIGS. 6-8. The impedance 530 increases during any respiratory inspiration 630, 730 and decreases during any respiratory expiration 650, 750. As before, the impedance signal 500 is also proportional to the amount of air inhaled, denoted the tidal volume 540, illustrated on the abscissa of the right side of the graph in FIGS. 6-8. The magnitude of variations in impedance and tidal volume during respiration are identifiable as the peak-to-peak variation of the impedance signal 500.

FIG. 6 illustrates respiration intervals used for disordered breathing detection and/or prediction useful in accordance with embodiments of the present invention. Detection of disordered breathing may involve defining and examining a number of respiratory cycle intervals. A respiration cycle is divided into an inspiration period 630 corresponding to the patient inhaling, an expiration period 650, corresponding to the patient exhaling, and a non-breathing period 660 occurring between inhaling and exhaling. Respiration intervals are established using an inspiration threshold 610 and an expiration threshold 620. The inspiration threshold 610 marks the beginning of an inspiration period 630 and is determined by the transthoracic impedance signal 500 rising above the inspiration threshold 610. The inspiration period 630 ends when the transthoracic impedance signal 500 is a maximum 640. The maximum transthoracic impedance signal 640 corresponds to both the end of the inspiration interval 630 and the beginning of an expiration interval 650. The expiration interval 650 continues until the transthoracic impedance 500 falls below an expiration threshold 620. A non-breathing interval 660 starts from the end of the expiration period 650 and continues until the beginning of a next inspiration period 670.

Detection of sleep apnea and severe sleep apnea is illustrated in FIG. 7. The patient's respiration signals are monitored and the respiration cycles are defined according to an inspiration 730, an expiration 750, and a non-breathing 760 interval as described in connection with FIG. 6. A condition of sleep apnea is detected when a non-breathing period 760 exceeds a first predetermined interval 790, denoted the sleep apnea interval. A condition of severe sleep apnea is detected when the non-breathing period 760 exceeds a second predetermined interval 795, denoted the severe sleep apnea interval. For example, sleep apnea may be detected when the non-breathing interval exceeds about 10 seconds, and severe sleep apnea may be detected when the non-breathing interval exceeds about 20 seconds. Similar to FIG. 6, the inspiration interval is denoted by 710 and the expiration interval is denoted by 720.

Hypopnea is a condition of disordered breathing characterized by abnormally shallow breathing. FIG. 8 is a graph of tidal volume derived from transthoracic impedance measurements. The graph of FIG. 8 illustrating the tidal volume of a hypopnea episode may be compared to the tidal volume of a normal breathing cycle illustrated previously in FIG. 5, which illustrated normal respiration tidal volume and rate. As shown in FIG. 8, hypopnea involves a period of abnormally shallow respiration, possible at an increased respiration rate.

Hypopnea is detected by comparing a patient's respiratory tidal volume 803 to a hypopnea tidal volume 801. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold for a predetermined minimum interval. Furthermore, various combinations of hypopnea cycles, breath intervals, and non-breathing intervals may be used to detect hypopnea, where the non-breathing intervals are determined as described above.

In FIG. 8, a hypopnea episode 805 is identified when the average tidal volume is significantly below the normal tidal volume. In the example illustrated in FIG. 8, the normal tidal volume during the breathing process is identified as the peak-to peak value identified as the respiratory tidal volume 803. The hypopnea tidal volume during the hypopnea episode 805 is identified as hypopnea tidal volume 801. For example, the hypopnea tidal volume 801 may be about 50% of the respiratory tidal volume 803. The value 50% is used by way of example only, and determination of thresholds for hypopnea events may be determined as any value appropriate for a given patient.

In the example above, if the tidal volume falls below 50% of the respiratory tidal volume 803, the breathing episode may be identified as a hypopnea event, originating the measurement of the hypopnea episode 805.

Cardiac stimulation may also be used as a therapy for disordered breathing, and may be combined with xPAP therapy and/or snoring detection systems and methods in accordance with embodiments of the present invention. Therapy methods for disordered breathing based on cardiac electrical stimulation are described in commonly owned U.S. Pat. No. 7,720,541, and U.S. Pat. No. 7,680,537, both of which are incorporated by reference herein. Disordered breathing detection and prediction systems and methods are further described in U.S. Pat. No. 7,189,204, U.S. Pat. No. 7,252,640, and U.S. Pat. No. 7,396,333, all of which are hereby incorporated by reference herein.

Figure 9:
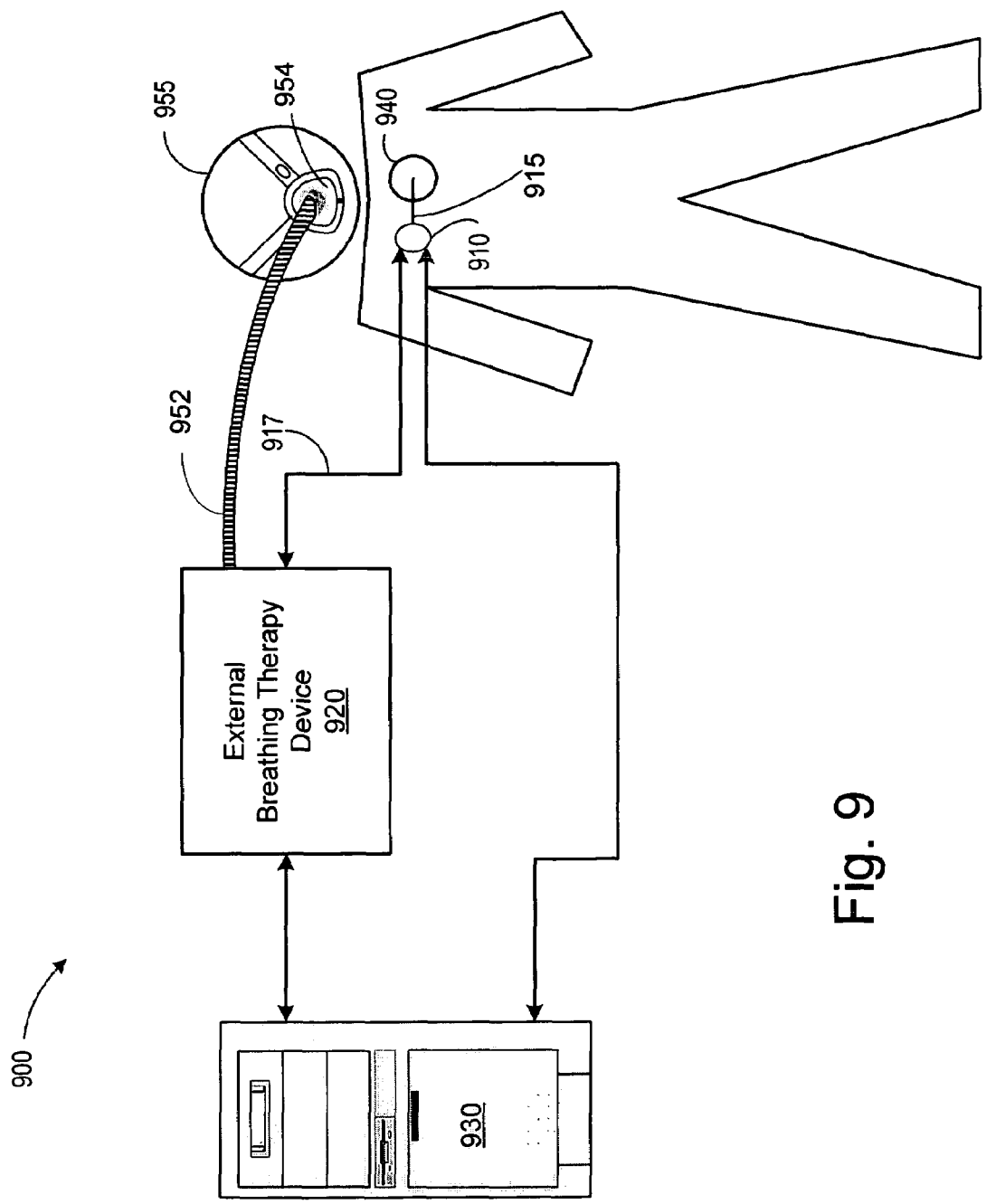
FIG. 9 illustrates a medical system including an implantable cardiac rhythm management device that cooperates with a patient-external respiration therapy device to provide coordinated patient monitoring, diagnosis and/or therapy in accordance with an embodiment of the present invention.

In the example illustrated in FIG. 9, a mechanical respiration therapy xPAP device 920 includes a positive airway pressure device that cooperates with a CRM 910, configured to modify the therapy of the xPAP device 920 using physiologic information acquired during non-sleep and provided by the CRM 910. The xPAP device 920 develops a positive air pressure that is delivered to the patient's airway through a tube system 952 and a mask 954 connected to the xPAP device 920. Positive airway pressure devices are often used to treat disordered breathing. In one configuration, for example, the positive airway pressure provided by the xPAP device 920 acts as a pneumatic splint keeping the patient's airway open and reducing the severity and/or number of occurrences of disordered breathing due to airway obstruction.

The xPAP device 920 may directly control the delivery of respiration therapy to the patient, and may contribute to the control of the CRM device 910. In addition, the xPAP device 920 may provide a number of monitoring and/or diagnostic functions in relation to the respiratory system and/or other physiological systems.

The CRM and xPAP devices 910, 920 may communicate directly through a wireless communications link 917, for example. Alternatively, or additionally, the CRM 910 and xPAP device 920 devices may communicate with and/or through an APM such as the APM system 930, as will be described further below with reference to FIG. 12.

Although FIG. 9 illustrates a CRM device 910 used with an xPAP device 920 to provide coordinated patient monitoring, diagnosis and/or therapy, any number of patient-internal and patient-external medical devices may be included in a medical system in accordance with the present invention. For example, a drug delivery device, such as a drug pump or controllable nebulizer, may be included in the system 900. The drug delivery device may cooperate with either or both of the CRM device 910 and the xPAP device 920 and may contribute to the patient monitoring, diagnosis, and/or therapeutic functions of the medical system 900.

According to one embodiment of the present invention, illustrated in FIG. 9, a medical system 900 may include an implantable cardiac rhythm management device 910 that cooperates with a patient-external respiration therapy device 920 to provide coordinated patient monitoring, diagnosis and/or therapy. The CRM 910 may provide a first set of monitoring, diagnostic, and/or therapeutic functions to a patient 955. The CRM 910 may be electrically coupled to a patient's heart 940 through one or more cardiac electrodes 915 terminating in, on, or about the heart 940. The cardiac electrodes 915 may sense cardiac signals produced by the heart 940 and/or provide therapy to one or more heart chambers. For example, the cardiac electrodes 915 may deliver electrical stimulation to one or more heart 940 chambers, and/or to one or multiple sites within the heart 940 chambers. The CRM 910 may directly control delivery of one or more cardiac therapies, such as cardiac pacing, defibrillation, cardioversion, cardiac resynchronization, and/or other cardiac therapies, for example. In addition, the CRM 910 may facilitate the control of a mechanical respiration device 920. Further, the CRM 910 may perform various monitoring and/or diagnostic functions in relation to the cardiovascular system and/or other physiological systems.

Figure 10:
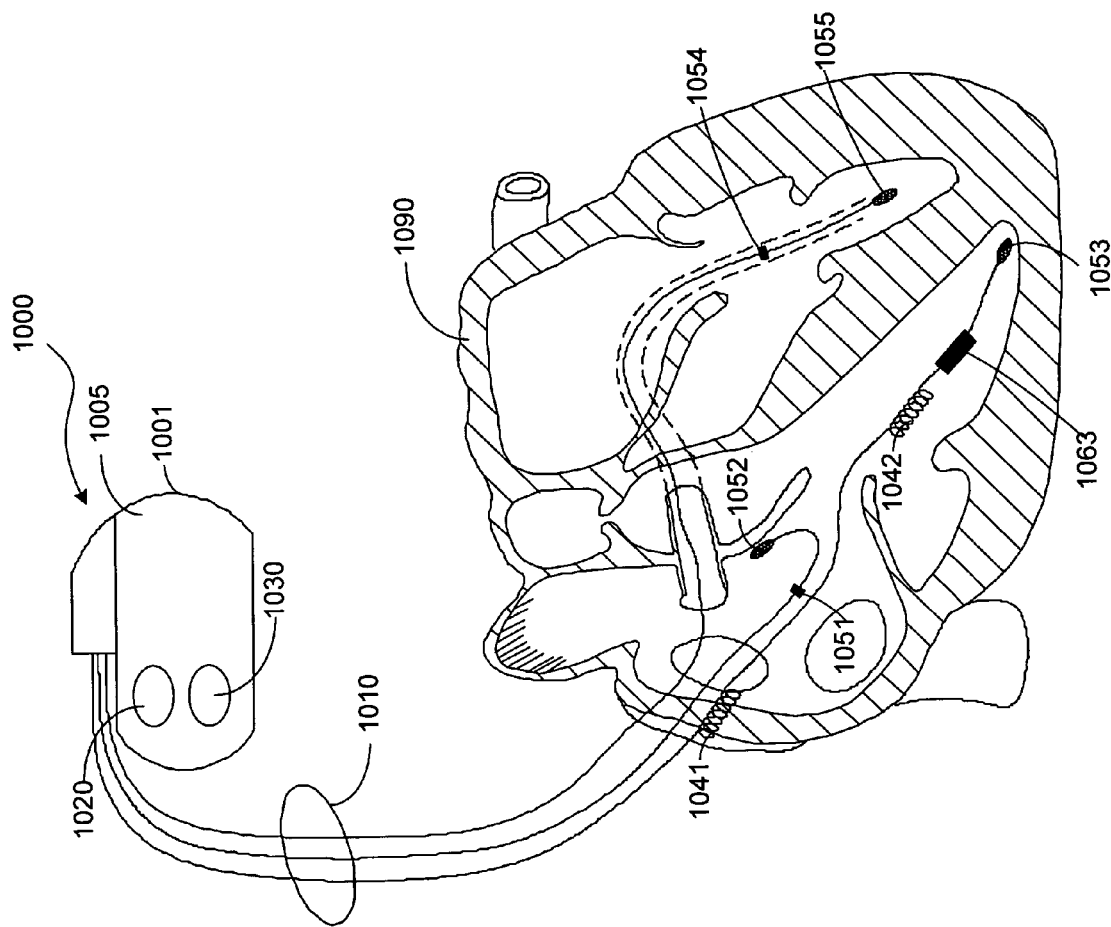
FIG. 10 is an illustration of an implantable cardiac device including a lead assembly shown implanted in a sectional view of a heart, the device used for coordinated patient monitoring, diagnosis, and/or therapy in accordance with embodiments of the present invention.

Referring now to FIG. 10, the implantable device illustrated in FIG. 10 is an embodiment of a PIMD that may benefit from modulated sleep-time therapy based on physiologic data acquired during non-sleep time in accordance with the present invention. In this example, the implantable device includes a cardiac rhythm management device (CRM) 1000 including an implantable pulse generator 1005 electrically and physically coupled to an intracardiac lead system 1010.

Portions of the intracardiac lead system 1010 are inserted into the patient's heart 1090. The intracardiac lead system 1010 includes one or more electrodes configured to sense electrical cardiac activity of the heart, deliver electrical stimulation to the heart, sense the patient's transthoracic impedance, and/or sense other physiological parameters, e,g, cardiac chamber pressure or temperature. Portions of the housing 1001 of the pulse generator 1005 may optionally serve as a can electrode.

Communications circuitry is disposed within the housing 1001 for facilitating communication between the pulse generator 1005 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 1005 may optionally incorporate a motion detector 1020 that may be used to sense various patient parameters and/or conditions. For example, the motion detector 1020 may be optionally configured to sense snoring, activity level, and/or chest wall movements associated with respiratory effort, for example. The motion detector 1020 may be implemented as an accelerometer positioned in or on the housing 1001 of the pulse generator 1005. If the motion sensor is implemented as an accelerometer, the motion sensor may also provide respiratory, e.g. rales, coughing, and cardiac, e.g. S1-S4 heart sounds, murmurs, and other acoustic information.

The lead system 1010 of the CRM 1000 may incorporate one or more transthoracic impedance sensors that may be used to acquire the patient's respiration waveform, or other respiration-related information. The transthoracic impedance sensor may include, for example, one or more intracardiac electrodes 1041, 1042, 1051-1055, 1063 positioned in one or more chambers of the heart 1090. The intracardiac electrodes 1041, 1042, 1051-1055, 1063 may be coupled to impedance drive/sense circuitry 1030 positioned within the housing of the pulse generator 1005.

In one implementation, impedance drive/sense circuitry 1030 generates a current that flows through the tissue between an impedance drive electrode 1051 and a can electrode on the housing 1001 of the pulse generator 1005. The voltage at an impedance sense electrode 1052 relative to the can electrode changes as the patient's transthoracic impedance changes. The voltage signal developed between the impedance sense electrode 1052 and the can electrode is detected by the impedance sense circuitry 1030. Other locations and/or combinations of impedance sense and drive electrodes are also possible.

The lead system 1010 may include one or more cardiac pace/sense electrodes 1051 through 1055 positioned in, on, or about one or more heart chambers for sensing electrical signals from the patient's heart 1090 and/or delivering pacing pulses to the heart 1090. The intracardiac sense/pace electrodes 1051 through 1055, such as those illustrated in FIG. 10, may be used to sense and/or pace one or more chambers of the heart, including the left ventricle, the right ventricle, the left atrium and/or the right atrium. The lead system 1010 may include one or more defibrillation electrodes 1041, 1042 for delivering defibrillation/cardioversion shocks to the heart.

The pulse generator 1005 may include circuitry for detecting cardiac arrhythmias and/or for controlling pacing or defibrillation therapy in the form of electrical stimulation pulses or shocks delivered to the heart through the lead system 1010. The pulse generator 1005 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference.

A PIMD may be used to implement various diagnostic functions, which may involve performing rate-based, pattern and rate-based, and/or morphological tachyarrhythmia discrimination analyses. Diagnostics functions may involve storing, trending, displaying, transmitting, and/or evaluating various indications based on the detection of snoring. Subcutaneous, cutaneous, and/or external sensors, such as those previously described, may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 11:
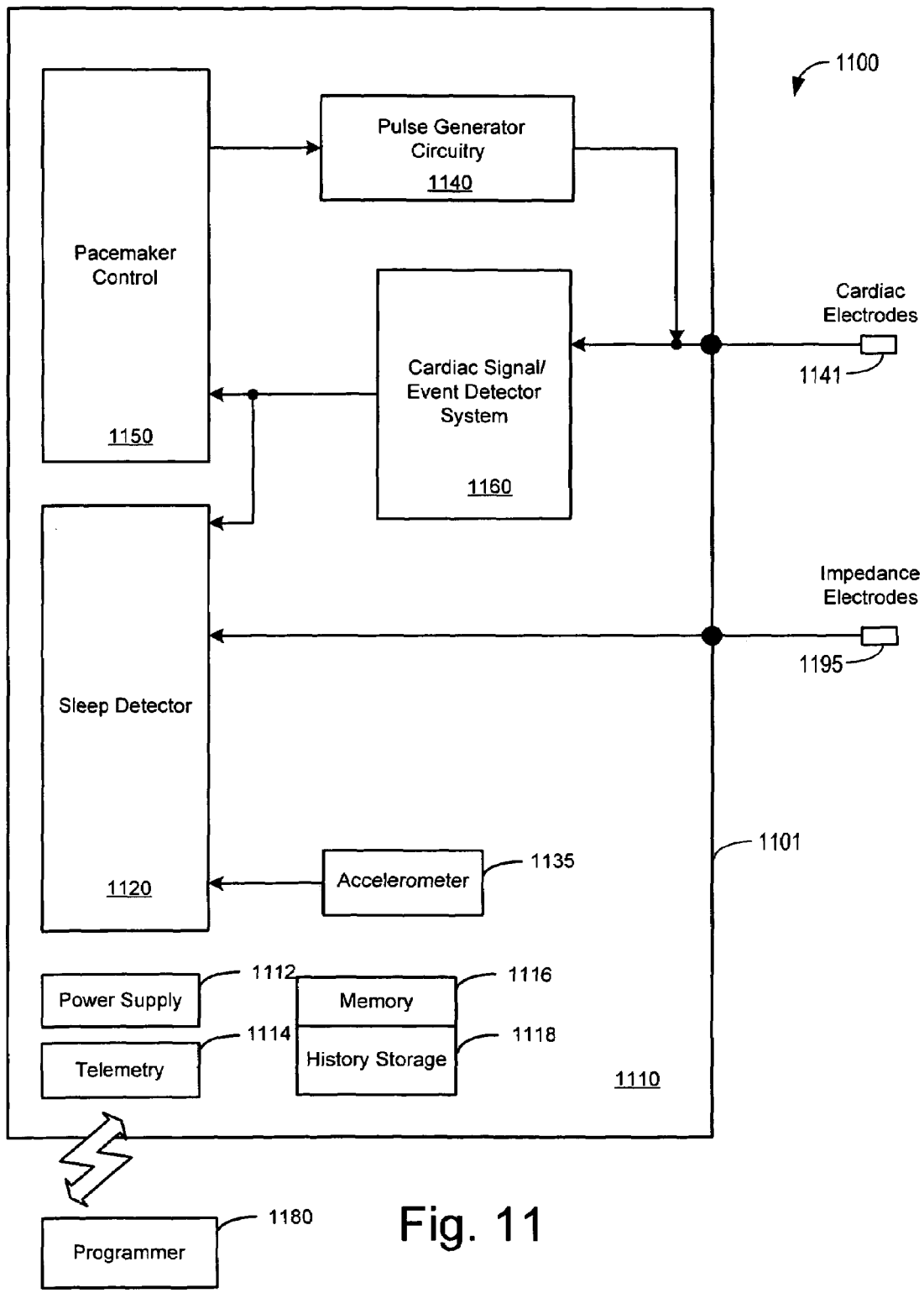
FIG. 11 is a block diagram of a cardiac rhythm management (CRM) system configured as a pacemaker and suitable for implementing a sleep detection methodology in accordance with embodiments of the present invention.

Referring now to FIG. 11, there is shown a block diagram of an embodiment of a PIMD 1100 configured as a pacemaker and suitable for implantably determining the presence of sleep disordered breathing and modifying sleep therapy based on physiologic data acquired during non-sleep in accordance with the present invention. FIG. 11 shows the PIMD 1100 divided into functional blocks. The PIMD 1100 includes a sleep detector 1120 for receiving sleep-related signals and detecting sleep in accordance with embodiments of the invention.

In one embodiment, the sleep detector 1120 is incorporated as part of CRM circuitry 1110 encased and hermetically sealed in a housing 1101 suitable for implanting in a human body. Power to the PIMD 1100 is supplied by an electrochemical battery power supply 1112 housed within the PIMD 1100. A connector block (not shown) is additionally attached to the PIMD 1100 to allow for the physical and electrical attachment of the cardiac lead system conductors to the CRM circuitry 1110.

The CRM circuitry 1110 may be configured as a programmable microprocessor-based system, with circuitry for detecting sleep in addition to providing pacing therapy to the heart. Cardiac signals sensed by one or more cardiac electrodes 1141 may be processed by the cardiac event detection circuitry 1160. Pace pulses controlled by the pacemaker control 1150 and generated by the pulse generator 1140 are delivered to the heart to treat various arrhythmias of the heart.

The memory circuit 1116 may store parameters for various device operations involved in sleep detection and/or cardiac pacing and sensing. The memory circuit 1116 may also store data indicative of sleep-related signals received by components of the CRM circuitry 1110, such as information derived from one or more impedance electrodes 1195, the cardiac signal detector system 1160, the accelerometer 1135, and/or the sleep detector 1120.

As illustrated in FIG. 11, the sleep detector 1120 receives signals derived from the cardiac event detector 1160, the impedance electrodes 1195 and the accelerometer 1135 to perform operations involving detecting sleep onset and sleep termination according to the principles of the present invention. Historical data storage 1118 may be coupled to the sleep detection circuitry 1120 for storing historical sleep related data. Such data may be transmitted to an external programmer unit 1180 and used for various diagnostic purposes and as needed or desired.

Telemetry circuitry 1114 is coupled to the CRM circuitry 1110 to allow the PIMD 1100 to communicate with a remote device such as the programmer 1180, or other device. In one embodiment, the telemetry circuitry 1114 and the programmer 1180 use a wire loop antenna and a radio frequency telemetric link to receive and transmit signals and data between the programmer 1180 and telemetry circuitry 1114. In this manner, programming commands and data may be transferred between the CRM circuitry 1110 and the one or more remote devices 1180 during and after implant.

The programming commands allow a physician to set or modify various parameters used by the CRM system 1100. These parameters may include setting sleep detection parameters for use during sleep detection, such as which sleep-related signals are to be used for sleep detection and threshold adjustment, and the initial sleep detection thresholds. In addition, the CRM system 1100 may download to the programmer 1180 stored data pertaining to sensed sleep periods, including the amount of time spent sleeping, the time of day sleep periods occurred, historical data of sleep times, and the number of arousals during the sleep periods, for example.

Still referring to FIG. 11, signals associated with patient activity may be detected through the use of an accelerometer 1135 positioned within the housing 1101 of the PIMD 1100. The accelerometer 1135 may be responsive to patient activity. The accelerometer signal may be correlated with activity level or workload, for example. Signals derived from the accelerometer 1135 are coupled to the sleep detector 1120 and may also be used by the pacemaker 1150 for implementing a rate adaptive pacing regimen, for example.

The impedance electrodes 1195 sense the patient's transthoracic impedance. The transthoracic impedance may be used to calculate various parameters associated with respiration. Impedance driver circuitry (not shown) induces a current that flows through the blood between the impedance drive electrode and a can electrode on the housing 1101 of the PIMD 1100. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1120 for further processing.

FIG. 12 is a block diagram of a medical system 1200 that may be used to implement moderated therapy delivered during sleep using physiological data acquired during non-sleep in accordance with embodiments of the invention. The medical system 1200 may include, for example, one or more patient-internal medical devices 1210 and one or more patient-external medical devices 1220. Each of the patient-internal 1210 and patient-external 1220 medical devices may include one or more of a patient monitoring unit 1212, 1222, a diagnostics unit 1214, 1224, and/or a therapy unit 1216, 1226.

The patient-internal medical device 1210 is typically a fully or partially implantable device that performs measuring, monitoring, diagnosis, and/or therapy functions. The patient-external medical device 1220 performs monitoring, diagnosis and/or therapy functions external to the patient (i.e., not invasively implanted within the patient's body). The patient-external medical device 1220 may be positioned on the patient, near the patient, or in any location external to the patient. It is understood that a portion of a patient-external medical device 1220 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1210, 1220 may be coupled to one or more sensors 1241, 1242, 1245, 1246, patient input devices 1243, 1247 and/or other information acquisition devices 1244, 1248. The sensors 1241, 1242, 1245, 1246, patient input devices 1243, 1247, and/or other information acquisition devices 1244, 1248 may be employed to detect conditions relevant to the monitoring, diagnostic, and/or therapeutic functions of the patient-internal and patient-external medical devices 1210, 1220.

The medical devices 1210, 1220 may each be coupled to one or more patient-internal sensors 1241, 1245 that are fully or partially implantable within the patient. The medical devices 1210, 1220 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1241 may be coupled to the patient-internal medical device 1210 through one or more internal leads 1253. Still referring to FIG. 12, one or more patient-internal sensors 1241 may be equipped with transceiver circuitry to support wireless communications between the one or more patient-internal sensors 1241 and the patient-internal medical device 1210 and/or the patient-external medical device 1220.

The patient-external sensors 1242 may be coupled to the patient-internal medical device 1210 and/or the patient-external medical device 1220 through one or more internal leads 1255 or through wireless connections. Patient-external sensors 1242 may communicate with the patient-internal medical device 1210 wirelessly. Patient-external sensors 1246 may be coupled to the patient-external medical device 1220 through one or more internal leads 1257 or through a wireless link.

The medical devices 1210, 1220 may be coupled to one or more patient input devices 1243, 1247. The patient input devices are used to allow the patient to manually transfer information to the medical devices 1210, 1220. The patient input devices 1243, 1247 may be particularly useful for inputting information concerning patient perceptions, such as how well the patient feels, and information such as patient smoking, drug use, or other activities that are not automatically sensed or detected by the medical devices 1210, 1220.

The medical devices 1210, 1220 may be connected to one or more information acquisition devices 1244, 1248, for example, a database that stores information useful in connection with the monitoring, diagnostic, or therapy functions of the medical devices 1210, 1220. For example, one or more of the medical devices 1210, 1220 may be coupled through a network to a patient information server 1230 that provides information about environmental conditions affecting the patient, e.g., the pollution index for the patient's location.

In one embodiment, the patient-internal medical device 1210 and the patient-external medical device 1220 may communicate through a wireless link between the medical devices 1210, 1220. For example, the patient-internal and patient-external devices 1210, 1220 may be coupled through a short-range radio link, such as Bluetooth, IEEE 802.11, and/or a proprietary wireless protocol. The communications link may facilitate unidirectional or bidirectional communication between the patient-internal 1210 and patient-external 1220 medical devices. Data and/or control signals may be transmitted between the patient-internal 1210 and patient-external 1220 medical devices to coordinate the functions of the medical devices 1210, 1220.

In another embodiment, the patient-internal and patient-external medical devices 1210, 1220 may be used within the structure of an advanced patient management system 1240. Advanced patient management systems 1240 involve a system of medical devices that are accessible through various communications technologies. For example, patient data may be downloaded from one or more of the medical devices periodically or on command, and stored at the patient information server 1230. The physician and/or the patient may communicate with the medical devices and the patient information server 1230, for example, to acquire patient data or to initiate, terminate or modify therapy.

The data stored on the patient information server 1230 may be accessible by the patient and the patient's physician through one or more terminals 1250, e.g., remote computers located in the patient's home or the physician's office. The patient information server 1230 may be used to communicate to one or more of the patient-internal and patient-external medical devices 1210, 1220 to provide remote control of the monitoring, diagnosis, and/or therapy functions of the medical devices 1210, 1220.

In one embodiment, the patient's physician may access patient data transmitted from the medical devices 1210, 1220 to the patient information server 1230. After evaluation of the patient data, the patient's physician may communicate with one or more of the patient-internal or patient-external devices 1210, 1220 through the APM system 1240 to initiate, terminate, or modify the monitoring, diagnostic, and/or therapy functions of the patient-internal and/or patient-external medical systems 1210, 1220. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1210, 1220 may not communicate directly, but may communicate indirectly through the APM system 1240. In this embodiment, the APM system 1240 may operate as an intermediary between two or more of the medical devices 1210, 1220. For example, data and/or control information may be transferred from one of the medical devices 1210, 1220 to the APM system 1240. The APM system 1240 may transfer the data and/or control information to another of the medical devices 1210, 1220.

In one embodiment, the APM system 1240 may communicate directly with the patient-internal and/or patient-external medical devices 1210, 1220. In another embodiment, the APM system 1240 may communicate with the patient-internal and/or patient-external medical devices 1210, 1220 through medical device programmers 1260, 1270 respectively associated with each medical device 1210, 1220.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings) may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
   acquiring data associated with a patient while the patient is awake, the data comprising respiration data indicative of a respiratory disorder; and
   adjusting a therapy delivered by a patient-external device to the patient during patient sleep, the adjustment based at least in part on the acquired data including the respiration data indicative of the respiratory disorder, the therapy comprising one or both of a respiratory therapy and a therapy to treat a sleep-related respiratory disorder associated with the respiratory disorder.

2. The method of claim 1, wherein the therapy comprises a positive airway pressure therapy.

3. The method of claim 1, wherein the therapy comprises a sleep disordered breathing therapy.

4. The method of claim 1, wherein the acquired data is acquired by an implantable cardiac rhythm management device.

5. The method of claim 1, wherein the therapy comprises a medication use or delivery therapy.

6. The method of claim 1, wherein adjusting the therapy comprises performing therapy titration using the acquired data.

7. The method of claim 1, further comprising detecting a pathological condition using the acquired data, and adjusting the therapy in response to the detected pathological condition.

8. The method of claim 1, wherein the acquired respiratory data indicative of the respiratory disorder is indicative of Cheyne-Stokes patterned breathing.

9. The method of claim 1, wherein the acquired data indicative of the respiratory disorder comprises one or more of breathing pattern data, breathing rate data, and transthoracic impedance data.

10. The method of claim 1, wherein the acquired data further comprises one or more of heart rate data, heart rate variability data, PR interval data, and cardiac arrhythmia data, and the therapy adjustment is further based on the acquired one or more of heart rate data, heart rate variability data, PR interval data, and cardiac arrhythmia data.

11. The method of claim 1, wherein the acquired data further comprises patient activity data, and the therapy adjustment is further based on the patient activity data.

12. The method of claim 1, wherein the respiratory disorder of the acquired respiratory data comprises a respiratory condition that occurs during non-sleep periods and results from the sleep-related respiratory disorder.

13. The method of claim 1, wherein the acquired data further comprises contextual data impacting the patient, and the therapy adjustment is further based on the contextual data impacting the patient.

14. The method of claim 1, wherein the acquired data indicates one or more of a rate of change of a respiratory condition associated with the respiratory disorder and an effect of the therapy in addressing the sleep-related respiratory disorder.

15. The method of claim 1, wherein the acquired data further comprises autonomic nervous system activity data, and the therapy adjustment is further based on the autonomic nervous activity data.

16. The method of claim 1, wherein the acquired data further comprises medication use data, and the therapy adjustment is further based on the medication use data.

17. The method of claim 1, wherein the acquired data further comprises one or both of blood pressure data and blood oxygen level data, and the therapy adjustment is further based on the one or both of blood pressure data or blood oxygen data.

18. A system, comprising:
    a data acquisition unit configured to acquire respiration data indicative of a respiratory disorder associated with a patient while the patient is awake; and
    a patient-external therapy delivery system configured to adjust a therapy delivered to the patient during patient sleep using the acquired respiration data indicative of the respiratory disorder, the therapy comprising one or both of a respiratory therapy and a therapy to treat a sleep-related respiratory disorder associated with the respiratory disorder.

19. The system of claim 18, wherein the data acquisition unit is further configured for implantation and to patient-internally monitor electrical cardiac activity of the patient.

20. The system of claim 18, wherein the data acquisition unit is further configured for implantation, to monitor electrical cardiac activity of the patient, and to deliver an electrical cardiac therapy to the patient.

21. The system of claim 18, wherein the therapy delivery system comprises a positive airway pressure device.

22. The system of claim 18, wherein the data acquisition unit is an implantable cardiac rhythm management device and the therapy delivery system comprises a positive airway pressure device.

23. The system of claim 18, wherein the therapy delivery system comprises a patient management system configured to communicate medication use data to the patient.

24. The system of claim 18, wherein the therapy delivery system comprises a drug delivery system.

25. The system of claim 18, wherein the data acquisition unit comprises one or more sensors for detecting a pathological condition, and wherein the acquired respiration data comprises a pathological respiration condition associated with the respiratory disorder.

26. The system of claim 18, wherein the data acquisition unit comprises a cardiac rhythm management device.

27. The system of claim 18, wherein the data acquisition unit comprises a respiratory therapy delivery device.

28. A system, comprising:

means for acquiring data associated with a patient while the patient is awake, the data comprising respiration data indicative of a respiratory disorder; and means for adjusting a therapy delivered by a patient-external device to the patient during patient sleep, the adjustment based at least in part on the acquired data including the respiration data indicative of the respiratory disorder, the therapy comprising one or both of a respiratory therapy and a therapy to treat a sleep-related respiratory disorder associated with the respiratory disorder.

* * * * *